US009381230B2

(12) United States Patent
Poelstra et al.

(10) Patent No.: US 9,381,230 B2
(45) Date of Patent: Jul. 5, 2016

(54) INTERFERON ANALOGS

(75) Inventors: Klaas Poelstra, Groningen (NL); Jai Prakash, Groningen (NL); Eleonora Beljaars, Groningen (NL); Ruchi Bansal, Groningen (NL)

(73) Assignee: BiOrion Technologies, B.V., Groningen (NL)

( * ) Notice: Subject to any disclaimer, the term of this patent is extended or adjusted under 35 U.S.C. 154(b) by 570 days.

(21) Appl. No.: 13/519,808

(22) PCT Filed: Dec. 30, 2010

(86) PCT No.: PCT/NL2010/050897
§ 371 (c)(1), (2), (4) Date: Oct. 10, 2012

(87) PCT Pub. No.: WO2011/081523
PCT Pub. Date: Jul. 7, 2011

(65) Prior Publication Data

US 2013/0064791 A1 Mar. 14, 2013

Related U.S. Application Data

(60) Provisional application No. 61/302,973, filed on Feb. 10, 2010.

(30) Foreign Application Priority Data

Dec. 31, 2009 (EP) .................................... 09181049

(51) Int. Cl.

| | |
|---|---|
| ***A61K 38/21*** | (2006.01) |
| ***C07K 14/555*** | (2006.01) |
| ***C07K 14/57*** | (2006.01) |
| ***A61K 38/12*** | (2006.01) |
| ***C07K 5/083*** | (2006.01) |
| ***C07K 5/09*** | (2006.01) |
| ***C07K 5/093*** | (2006.01) |

(52) U.S. Cl.
CPC ............... *A61K 38/217* (2013.01); *A61K 38/12* (2013.01); *A61K 38/21* (2013.01); *C07K 5/081* (2013.01); *C07K 5/0808* (2013.01); *C07K 5/0817* (2013.01); *C07K 5/0819* (2013.01); *C07K 14/555* (2013.01); *C07K 14/57* (2013.01)

(58) Field of Classification Search
None
See application file for complete search history.

(56) References Cited

U.S. PATENT DOCUMENTS

| | | | | |
|---|---|---|---|---|
| 5,770,191 | A | 6/1998 | Johnson et al. | 424/85.5 |
| 6,120,762 | A | 9/2000 | Johnson et al. | 424/85.5 |
| 7,390,875 | B2 | 6/2008 | Bonnet et al. | 530/345 |

FOREIGN PATENT DOCUMENTS

| | | | |
|---|---|---|---|
| WO | WO 00/23113 | 4/2000 | A61K 47/48 |
| WO | WO 02/20558 | 3/2002 | C07K 1/107 |
| WO | WO 2004/005341 | 1/2004 | C07K 14/555 |
| WO | WO 2008/068621 | 6/2008 | A61K 45/06 |

OTHER PUBLICATIONS

Kolchanov, 1988, Journal of Molecular Evolution, vol. 27, pp. 154-162.*
Pasquo, 2012, PLoS ONE, vol. 7, Issue 2, e32555.*
Bork, 2000, Genome Research 10:398-400.*
Bork et al., 1996, Trends in Genetics 12:425-427.*
Ahmed et al., "Peptide Mimetics of Gamma Interferon Possess Anti-viral Properties against Vaccinia Virus and Other Viruses in the Presence of Poxvirus B8R Protein," Journal of Virology, vol. 79, No. 9, May 2005, pp. 5632-5639.
Ahmed et al., "IFN Mimetic as a Therapeutic for Lethal Vaccinia Virus Infection: Possible Effects on Innate and Adaptive Immune Responses," The Journal of Immunology, vol. 178, 2007, pp. 4576-4583.
Beljaars et al., "The preferential homing of a platelet derived growth factor receptor-recognizing macromolecule to fibroblast-like cells in fibrotic tissue," Biochemical Pharmacology, vol. 66, 2003, pp. 1307-1317.
Hagens et al., "Targeting 15d-Prostaglandin $J_2$ to Hepatic Stellate Cells: Two Options Evaluated," Pharmaceutical Research, vol. 24, No. 3, Mar. 2007, pp. 566-574.
Subramaniam et al., "The COOH-terminal nuclear localization sequence of interferon gamma regulates STAT1α nuclear translocation of an intracellular site," Journal of Cell Science, vol. 113, 2000, pp. 2771-2781.
Temming et al., "RGD-based strategies for selective delivery of therapeutics and imaging agents to the tumour vasculature," Drug Resistance Updates, vol. 8, 2005, pp. 381-402.
International Search Authority, International Search Report—International Application No. PCT/NL2010/050897, dated Jun. 7, 2011, together with the Written Opinion of the International Searching Authority, 19 pages.

* cited by examiner

*Primary Examiner* — Christine J Saoud
*Assistant Examiner* — Jegatheesan Seharaseyon
(74) *Attorney, Agent, or Firm* — Sunstein Kann Murphy & Timbers LLP

(57) ABSTRACT

The invention relates to the field of medicine. Among others, it relates to biologically active analogs of interferons (IFNs) which show less unwanted side-effects and to the therapeutic uses thereof. Provided is an IFN analog, wherein the moiety mediating binding to its natural receptor is at least functionally disrupted and wherein the analog comprises a signaling moiety capable of mediating intracellular IFN activity, said signaling moiety being provided at its N-terminus, optionally via a linker, with at least one targeting domain capable of binding to a cell surface receptor other than the IFN receptor.

3 Claims, 12 Drawing Sheets

BiPPB sequence (23 amino acids)

Figure 1:
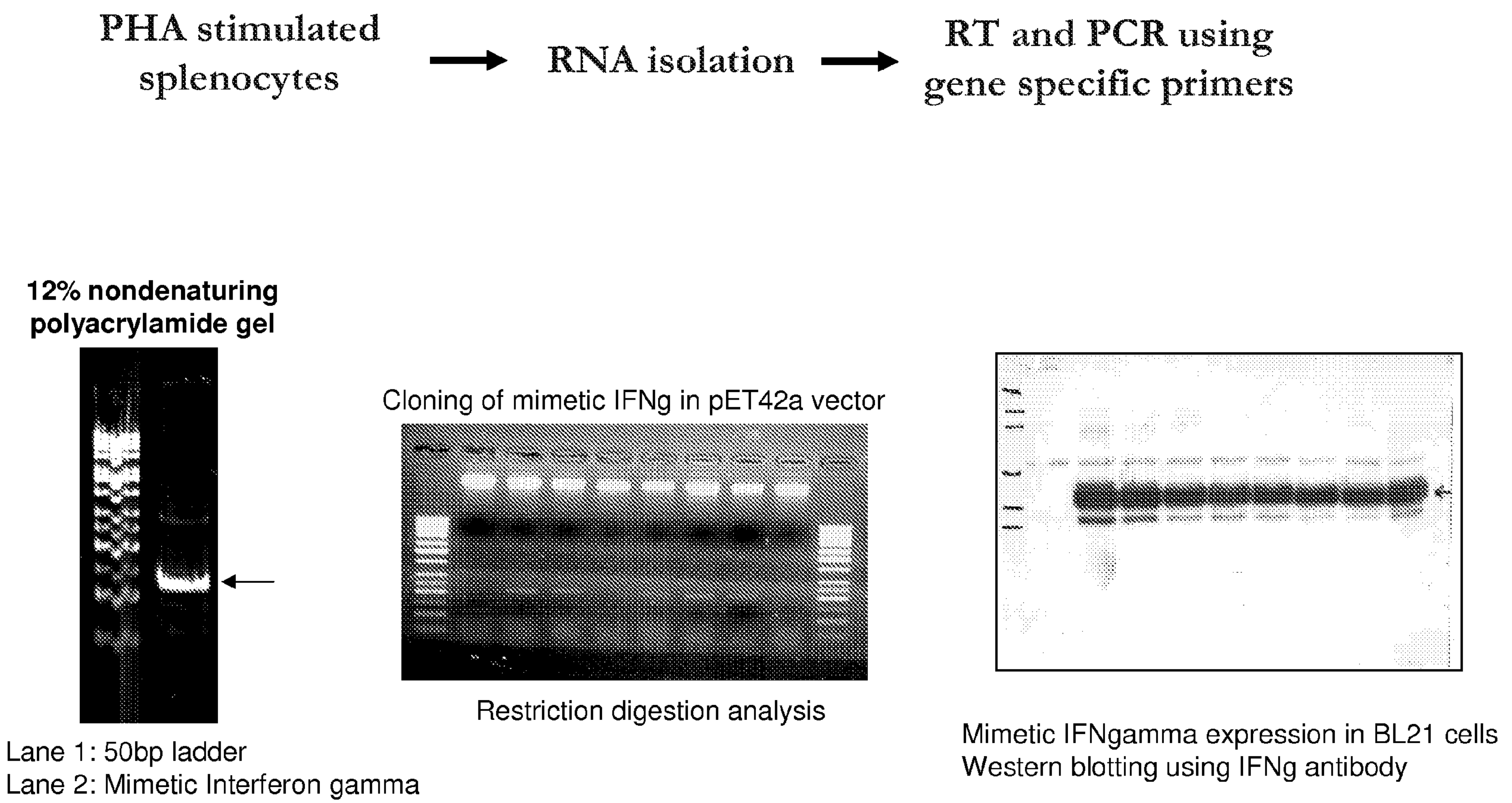

cys ser arg asn leu Ile asp cys lys gly ser gly ser gly gly cys ser arg asn leu Ile asp cys * (SEQ ID NO:65)
TGT TCG CGG AAC CTC ATC GAT TGT AAG GGA TCC GGA GGT TGT TCA CGT AAT CTA ATA GAT TGT GAT TGT TTA (SEQ ID NO: 66)

SEQUENCE LISTING

<160> NUMBER OF SEQ ID NOS: 66

<210> SEQ ID NO 1
<211> LENGTH: 7
<212> TYPE: PRT
<213> ORGANISM: Artificial
<220> FEATURE:
<223> OTHER INFORMATION: polybasic NLS motif
<220> FEATURE:
<221> NAME/KEY: misc_feature
<222> LOCATION: (4)..(4)
<223> OTHER INFORMATION: Xaa can be any amino acid residue

<400> SEQUENCE: 1

Arg Lys Arg Xaa Arg Ser Arg
1               5

<210> SEQ ID NO 2
<211> LENGTH: 7
<212> TYPE: PRT
<213> ORGANISM: Artificial
<220> FEATURE:
<223> OTHER INFORMATION: polybasic NLS motif

<400> SEQUENCE: 2

Arg Lys Arg Lys Arg Ser Arg
1               5

<210> SEQ ID NO 3
<211> LENGTH: 6
<212> TYPE: PRT
<213> ORGANISM: Artificial
<220> FEATURE:
<223> OTHER INFORMATION: polybasic NLS motif

<400> SEQUENCE: 3

Lys Ser Lys Arg Ser Arg
1               5

<210> SEQ ID NO 4
<211> LENGTH: 5
<212> TYPE: PRT
<213> ORGANISM: Artificial
<220> FEATURE:
<223> OTHER INFORMATION: polybasic NLS motif

<400> SEQUENCE: 4

Lys Arg Thr Arg Ser
1               5

<210> SEQ ID NO 5
<211> LENGTH: 6
<212> TYPE: PRT
<213> ORGANISM: Artificial
<220> FEATURE:
<223> OTHER INFORMATION: polybasic NLS motif

<400> SEQUENCE: 5

Lys Arg Thr Arg Ser Gln
1               5

<210> SEQ ID NO 6
<211> LENGTH: 37
<212> TYPE: PRT
<213> ORGANISM: Artificial
<220> FEATURE:
<223> OTHER INFORMATION: IFN signaling moiety

<400> SEQUENCE: 6

Lys Phe Glu Val Asn Asn Pro Gln Val Gln Arg Gln Ala Phe Asn Glu
1 5 10 15

Leu Ile Arg Val Val His Gln Leu Leu Pro Glu Ser Ser Leu Arg Lys
20 25 30

Arg Lys Arg Ser Arg
35

<210> SEQ ID NO 7
<211> LENGTH: 36
<212> TYPE: PRT
<213> ORGANISM: Artificial
<220> FEATURE:
<223> OTHER INFORMATION: IFN signaling moiety

<400> SEQUENCE: 7

Tyr Ser Val Thr Asp Leu Asn Val Gln Arg Lys Ala Ile His Glu Leu
1 5 10 15

Ile Gln Val Met Ala Glu Leu Ser Pro Ala Ala Lys Thr Gly Lys Arg
20 25 30

Thr Arg Ser Gln
35

<210> SEQ ID NO 8
<211> LENGTH: 36
<212> TYPE: PRT
<213> ORGANISM: Artificial
<220> FEATURE:
<223> OTHER INFORMATION: IFN signaling moiety

<400> SEQUENCE: 8

Tyr Ser Val Thr Asp Leu Asn Val Gln Arg Lys Ala Ile His Glu Leu
1 5 10 15

Ile Gln Val Met Ala Glu Leu Ser Pro Ala Ala Lys Thr Gly Lys Arg
20 25 30

Lys Arg Ser Gln
35

<210> SEQ ID NO 9
<211> LENGTH: 39
<212> TYPE: PRT
<213> ORGANISM: Artificial
<220> FEATURE:
<223> OTHER INFORMATION: IFN signaling moiety

<400> SEQUENCE: 9

Ala Lys Phe Glu Val Asn Asn Pro Gln Ile Gln His Lys Ala Val Asn
1 5 10 15

Glu Leu Ile Arg Val Ile His Gln Leu Ser Pro Glu Ser Ser Leu Arg
20 25 30

Lys Arg Lys Arg Ser Arg Cys
35

<210> SEQ ID NO 10
<211> LENGTH: 33
<212> TYPE: PRT
<213> ORGANISM: Artificial
<220> FEATURE:
<223> OTHER INFORMATION: consensus signaling moiety
<220> FEATURE:
<221> NAME/KEY: misc_feature
<222> LOCATION: (2)..(5)
<223> OTHER INFORMATION: Xaa can be any amino acid residue
<220> FEATURE:
<221> NAME/KEY: misc_feature
<222> LOCATION: (9)..(9)
<223> OTHER INFORMATION: Xaa can be any amino acid residue
<220> FEATURE:
<221> NAME/KEY: misc_feature
<222> LOCATION: (11)..(12)
<223> OTHER INFORMATION: Xaa can be any amino acid residue
<220> FEATURE:
<221> NAME/KEY: misc_feature
<222> LOCATION: (16)..(16)
<223> OTHER INFORMATION: Xaa can be any amino acid residue
<220> FEATURE:
<221> NAME/KEY: misc_feature
<222> LOCATION: (18)..(20)
<223> OTHER INFORMATION: Xaa can be any amino acid residue
<220> FEATURE:
<221> NAME/KEY: misc_feature
<222> LOCATION: (22)..(22)
<223> OTHER INFORMATION: Xaa can be any amino acid residue
<220> FEATURE:
<221> NAME/KEY: misc_feature
<222> LOCATION: (24)..(28)
<223> OTHER INFORMATION: Xaa can be any amino acid residue
<220> FEATURE:
<221> NAME/KEY: misc_feature
<222> LOCATION: (31)..(31)
<223> OTHER INFORMATION: Xaa can be any amino acid residue

<400> SEQUENCE: 10

```
Val Xaa Xaa Xaa Xaa Val Gln Arg Xaa Ala Xaa Xaa Glu Leu Ile Xaa
1               5                   10                  15

Val Xaa Xaa Xaa Leu Xaa Pro Xaa Xaa Xaa Xaa Xaa Lys Arg Xaa Arg
            20                  25                  30

Ser
```

<210> SEQ ID NO 11
<211> LENGTH: 33
<212> TYPE: PRT
<213> ORGANISM: Artificial
<220> FEATURE:
<223> OTHER INFORMATION: consensus sequence
<220> FEATURE:
<221> NAME/KEY: misc_feature
<222> LOCATION: (2)..(6)
<223> OTHER INFORMATION: Xaa can be any amino acid residue
<220> FEATURE:
<221> NAME/KEY: misc_feature
<222> LOCATION: (8)..(9)
<223> OTHER INFORMATION: Xaa can be any amino acid residue
<220> FEATURE:
<221> NAME/KEY: misc_feature
<222> LOCATION: (11)..(12)
<223> OTHER INFORMATION: Xaa can be any amino acid residue
<220> FEATURE:
<221> NAME/KEY: misc_feature
<222> LOCATION: (16)..(16)
<223> OTHER INFORMATION: Xaa can be any amino acid residue
<220> FEATURE:
<221> NAME/KEY: misc_feature
<222> LOCATION: (18)..(20)
<223> OTHER INFORMATION: Xaa can be any amino acid residue
<220> FEATURE:
<221> NAME/KEY: misc_feature
<222> LOCATION: (22)..(22)
<223> OTHER INFORMATION: Xaa can be any amino acid residue
<220> FEATURE:
<221> NAME/KEY: misc_feature
<222> LOCATION: (24)..(28)
<223> OTHER INFORMATION: Xaa can be any amino acid residue

<400> SEQUENCE: 11

```
Val Xaa Xaa Xaa Xaa Xaa Gln Xaa Xaa Ala Xaa Xaa Glu Leu Ile Xaa
1               5                   10                  15
```

-continued

```
Val Xaa Xaa Xaa Leu Xaa Pro Xaa Xaa Xaa Xaa Xaa Lys Arg Lys Arg
            20                  25                  30

Ser


<210> SEQ ID NO 12
<211> LENGTH: 34
<212> TYPE: PRT
<213> ORGANISM: Artificial
<220> FEATURE:
<223> OTHER INFORMATION: consensus
<220> FEATURE:
<221> NAME/KEY: MOD_RES
<222> LOCATION: (2)..(5)
<223> OTHER INFORMATION: Xaa can be any amino acid residue
<220> FEATURE:
<221> NAME/KEY: MOD_RES
<222> LOCATION: (6)..(6)
<223> OTHER INFORMATION: may be Valine or Isoleucine
<220> FEATURE:
<221> NAME/KEY: MOD_RES
<222> LOCATION: (8)..(8)
<223> OTHER INFORMATION: may be arginine or histidine
<220> FEATURE:
<221> NAME/KEY: MOD_RES
<222> LOCATION: (9)..(9)
<223> OTHER INFORMATION: may be glutamine or lysine
<220> FEATURE:
<221> NAME/KEY: MOD_RES
<222> LOCATION: (11)..(11)
<223> OTHER INFORMATION: may be phenylalanine,valine or isoleucine
<220> FEATURE:
<221> NAME/KEY: MOD_RES
<222> LOCATION: (12)..(12)
<223> OTHER INFORMATION: may be asparagine or histidine
<220> FEATURE:
<221> NAME/KEY: MOD_RES
<222> LOCATION: (16)..(16)
<223> OTHER INFORMATION: may be arginine or glutamine
<220> FEATURE:
<221> NAME/KEY: MOD_RES
<222> LOCATION: (18)..(18)
<223> OTHER INFORMATION: Xaa can be any amino acid residue
<220> FEATURE:
<221> NAME/KEY: MOD_RES
<222> LOCATION: (19)..(19)
<223> OTHER INFORMATION: may be histidine or alanine
<220> FEATURE:
<221> NAME/KEY: MOD_RES
<222> LOCATION: (20)..(20)
<223> OTHER INFORMATION: may be glutamine or glutamic acid
<220> FEATURE:
<221> NAME/KEY: MOD_RES
<222> LOCATION: (22)..(22)
<223> OTHER INFORMATION: may be leucine or serine
<220> FEATURE:
<221> NAME/KEY: MOD_RES
<222> LOCATION: (24)..(24)
<223> OTHER INFORMATION: may be glutamic acid or alanine
<220> FEATURE:
<221> NAME/KEY: MOD_RES
<222> LOCATION: (25)..(25)
<223> OTHER INFORMATION: may be serine or alanine
<220> FEATURE:
<221> NAME/KEY: MOD_RES
<222> LOCATION: (26)..(26)
<223> OTHER INFORMATION: may be serine or alanine
<220> FEATURE:
<221> NAME/KEY: MOD_RES
<222> LOCATION: (27)..(27)
<223> OTHER INFORMATION: may be leucine or lysine
<220> FEATURE:
<221> NAME/KEY: MOD_RES
<222> LOCATION: (28)..(29)
<223> OTHER INFORMATION: Xaa can be any amino acid residue

<400> SEQUENCE: 12
```

```
Val Xaa Xaa Xaa Xaa Xaa Gln Xaa Xaa Ala Xaa Xaa Glu Leu Ile Xaa
1               5                   10                  15

Val Xaa Xaa Xaa Leu Xaa Pro Xaa Xaa Xaa Xaa Xaa Xaa Lys Arg Lys
            20                  25                  30

Arg Ser


<210> SEQ ID NO 13
<211> LENGTH: 14
<212> TYPE: PRT
<213> ORGANISM: Artificial
<220> FEATURE:
<223> OTHER INFORMATION: fragment signaling moiety

<400> SEQUENCE: 13

Leu Leu Pro Glu Ser Ser Leu Arg Lys Arg Lys Arg Ser Arg
1               5                   10


<210> SEQ ID NO 14
<211> LENGTH: 12
<212> TYPE: PRT
<213> ORGANISM: Artificial
<220> FEATURE:
<223> OTHER INFORMATION: fragment signaling moiety

<400> SEQUENCE: 14

Lys Phe Glu Val Asn Asn Pro Gln Val Gln Arg Gln
1               5                   10


<210> SEQ ID NO 15
<211> LENGTH: 14
<212> TYPE: PRT
<213> ORGANISM: Artificial
<220> FEATURE:
<223> OTHER INFORMATION: fragment signaling moiety

<400> SEQUENCE: 15

Gln Ala Phe Asn Glu Leu Ile Arg Val Val His Gln Leu Leu
1               5                   10


<210> SEQ ID NO 16
<211> LENGTH: 17
<212> TYPE: PRT
<213> ORGANISM: Artificial
<220> FEATURE:
<223> OTHER INFORMATION: fragment signaling moiety

<400> SEQUENCE: 16

Met Ala Glu Leu Ser Pro Ala Ala Lys Thr Gly Lys Arg Thr Arg Ser
1               5                   10                  15

Gln


<210> SEQ ID NO 17
<211> LENGTH: 13
<212> TYPE: PRT
<213> ORGANISM: Artificial
<220> FEATURE:
<223> OTHER INFORMATION: fragment signaling moiety

<400> SEQUENCE: 17

Tyr Ser Val Thr Asp Leu Asn Val Gln Arg Lys Ala Ile
1               5                   10


<210> SEQ ID NO 18
<211> LENGTH: 14
```

<212> TYPE: PRT
<213> ORGANISM: Artificial
<220> FEATURE:
<223> OTHER INFORMATION: fragment signaling moiety

<400> SEQUENCE: 18

Lys Ala Ile His Glu Leu Ile Gln Val Met Ala Glu Leu Ser
1 5 10

<210> SEQ ID NO 19
<211> LENGTH: 36
<212> TYPE: PRT
<213> ORGANISM: Homo sapiens

<400> SEQUENCE: 19

Tyr Ser Val Thr Asp Leu Asn Val Gln Arg Lys Ala Ile His Glu Leu
1 5 10 15

Ile Gln Val Met Ala Glu Leu Ser Pro Ala Ala Lys Thr Gly Lys Arg
20 25 30

Thr Arg Ser Gln
35

<210> SEQ ID NO 20
<211> LENGTH: 36
<212> TYPE: PRT
<213> ORGANISM: Mus musculus

<400> SEQUENCE: 20

Phe Glu Val Asn Asn Pro Gln Val Gln Arg Gln Ala Phe Asn Glu Leu
1 5 10 15

Ile Arg Val Val His Gln Leu Leu Pro Glu Ser Ser Leu Arg Lys Arg
20 25 30

Lys Arg Ser Arg
35

<210> SEQ ID NO 21
<211> LENGTH: 8
<212> TYPE: PRT
<213> ORGANISM: Artificial
<220> FEATURE:
<223> OTHER INFORMATION: targeting domain fragment
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 21

Xaa Ser Arg Asn Leu Ile Asp Xaa
1 5

<210> SEQ ID NO 22
<211> LENGTH: 18
<212> TYPE: PRT
<213> ORGANISM: Artificial
<220> FEATURE:
<223> OTHER INFORMATION: targeting domain short
<220> FEATURE:
<221> NAME/KEY: misc_feature
<222> LOCATION: (9)..(9)
<223> OTHER INFORMATION: Xaa can be any naturally occurring amino acid

<400> SEQUENCE: 22

Cys Ser Arg Asn Leu Ile Asp Cys Xaa Cys Ser Arg Asn Leu Ile Asp
1 5 10 15

Cys Ser

<210> SEQ ID NO 23
<211> LENGTH: 24
<212> TYPE: PRT
<213> ORGANISM: Artificial
<220> FEATURE:
<223> OTHER INFORMATION: targeting domain long
<220> FEATURE:
<221> NAME/KEY: misc_feature
<222> LOCATION: (9)..(15)
<223> OTHER INFORMATION: Xaa can be any naturally occurring amino acid

<400> SEQUENCE: 23

Cys Ser Arg Asn Leu Ile Asp Cys Xaa Xaa Xaa Xaa Xaa Xaa Xaa Cys
1 5 10 15

Ser Arg Asn Leu Ile Asp Cys Ser
20

<210> SEQ ID NO 24
<211> LENGTH: 22
<212> TYPE: PRT
<213> ORGANISM: Artificial
<220> FEATURE:
<223> OTHER INFORMATION: targeting domain

<400> SEQUENCE: 24

Cys Ser Arg Asn Leu Ile Asp Cys Lys Gly Ser Gly Gly Cys Ser Arg
1 5 10 15

Asn Leu Ile Asp Cys Ser
20

<210> SEQ ID NO 25
<211> LENGTH: 24
<212> TYPE: PRT
<213> ORGANISM: Artificial
<220> FEATURE:
<223> OTHER INFORMATION: targeting domain

<400> SEQUENCE: 25

Cys Ser Arg Asn Leu Ile Asp Cys Lys Gly Ser Gly Ser Gly Gly Cys
1 5 10 15

Ser Arg Asn Leu Ile Asp Cys Ser
20

<210> SEQ ID NO 26
<211> LENGTH: 22
<212> TYPE: PRT
<213> ORGANISM: Artificial
<220> FEATURE:
<223> OTHER INFORMATION: targeting domain

<400> SEQUENCE: 26

Cys Ser Arg Asn Leu Ile Asp Cys Gly Gly Gly Asp Gly Gly Cys Ser
1 5 10 15

Arg Asn Leu Ile Asp Cys
20

<210> SEQ ID NO 27
<211> LENGTH: 21
<212> TYPE: PRT
<213> ORGANISM: Artificial
<220> FEATURE:

<223> OTHER INFORMATION: targeting domain

<400> SEQUENCE: 27

```
Cys Ser Arg Asn Leu Ile Asp Cys Gly Gly Asp Gly Gly Cys Ser Arg
1               5                   10                  15

Asn Leu Ile Asp Cys
            20
```

<210> SEQ ID NO 28
<211> LENGTH: 21
<212> TYPE: PRT
<213> ORGANISM: Artificial
<220> FEATURE:
<223> OTHER INFORMATION: targeting domain

<400> SEQUENCE: 28

```
Cys Ser Arg Asn Leu Ile Asp Cys Gly Asp Asp Gly Gly Cys Ser Arg
1               5                   10                  15

Asn Leu Ile Asp Cys
            20
```

<210> SEQ ID NO 29
<211> LENGTH: 22
<212> TYPE: PRT
<213> ORGANISM: Artificial
<220> FEATURE:
<223> OTHER INFORMATION: targeting domain

<400> SEQUENCE: 29

```
Cys Ser Arg Asn Leu Ile Asp Cys Gly Gly Gly Gly Gly Gly Cys Ser
1               5                   10                  15

Arg Asn Leu Ile Asp Cys
            20
```

<210> SEQ ID NO 30
<211> LENGTH: 63
<212> TYPE: PRT
<213> ORGANISM: Artificial
<220> FEATURE:
<223> OTHER INFORMATION: interferon gamma analog

<400> SEQUENCE: 30

```
Cys Ser Arg Asn Leu Ile Asp Cys Lys Gly Ser Gly Gly Cys Ser Arg
1               5                   10                  15

Asn Leu Ile Asp Cys Ser Ala Ala Ala Ala Lys Phe Glu Val Asn Asn
            20                  25                  30

Pro Gln Val Gln Arg Gln Ala Phe Asn Glu Leu Ile Arg Val Val His
        35                  40                  45

Gln Leu Leu Pro Glu Ser Ser Leu Arg Lys Arg Lys Arg Ser Arg
    50                  55                  60
```

<210> SEQ ID NO 31
<211> LENGTH: 65
<212> TYPE: PRT
<213> ORGANISM: Artificial
<220> FEATURE:
<223> OTHER INFORMATION: interferon gamma analog

<400> SEQUENCE: 31

```
Cys Ser Arg Asn Leu Ile Asp Cys Lys Gly Ser Gly Ser Gly Gly Cys
1               5                   10                  15

Ser Arg Asn Leu Ile Asp Cys Ser Ala Ala Ala Ala Lys Phe Glu Val
            20                  25                  30
```

```
Asn Asn Pro Gln Val Gln Arg Gln Ala Phe Asn Glu Leu Ile Arg Val
        35                  40                  45

Val His Gln Leu Leu Pro Glu Ser Ser Leu Arg Lys Arg Lys Arg Ser
    50                  55                  60

Arg
65


<210> SEQ ID NO 32
<211> LENGTH: 63
<212> TYPE: PRT
<213> ORGANISM: Artificial
<220> FEATURE:
<223> OTHER INFORMATION: interferon gamma analog

<400> SEQUENCE: 32

Cys Ser Arg Asn Leu Ile Asp Cys Gly Gly Gly Asp Gly Gly Cys Ser
1               5                   10                  15

Arg Asn Leu Ile Asp Cys Ser Ala Ala Ala Lys Phe Glu Val Asn Asn
            20                  25                  30

Pro Gln Val Gln Arg Gln Ala Phe Asn Glu Leu Ile Arg Val Val His
        35                  40                  45

Gln Leu Leu Pro Glu Ser Ser Leu Arg Lys Arg Lys Arg Ser Arg
    50                  55                  60


<210> SEQ ID NO 33
<211> LENGTH: 8
<212> TYPE: PRT
<213> ORGANISM: Artificial
<220> FEATURE:
<223> OTHER INFORMATION: targeting domain fragment
<220> FEATURE:
<221> NAME/KEY: misc_feature
<222> LOCATION: (1)..(1)
<223> OTHER INFORMATION: Xaa can be any amino acid residue
<220> FEATURE:
<221> NAME/KEY: misc_feature
<222> LOCATION: (8)..(8)
<223> OTHER INFORMATION: Xaa can be any amino acid residue

<400> SEQUENCE: 33

Xaa Ser Arg Asn Leu Ile Asp Xaa
1               5


<210> SEQ ID NO 34
<211> LENGTH: 18
<212> TYPE: PRT
<213> ORGANISM: Artificial
<220> FEATURE:
<223> OTHER INFORMATION: targeting domain short
<220> FEATURE:
<221> NAME/KEY: misc_feature
<222> LOCATION: (1)..(1)
<223> OTHER INFORMATION: Xaa can be any amino acid residue
<220> FEATURE:
<221> NAME/KEY: misc_feature
<222> LOCATION: (8)..(11)
<223> OTHER INFORMATION: Xaa can be any amino acid residue
<220> FEATURE:
<221> NAME/KEY: misc_feature
<222> LOCATION: (18)..(18)
<223> OTHER INFORMATION: Xaa can be any amino acid residue

<400> SEQUENCE: 34

Xaa Ser Arg Asn Leu Ile Asp Xaa Xaa Xaa Xaa Ser Arg Asn Leu Ile
1               5                   10                  15

Asp Xaa
```

<210> SEQ ID NO 35
<211> LENGTH: 23
<212> TYPE: PRT
<213> ORGANISM: Artificial
<220> FEATURE:
<223> OTHER INFORMATION: targeting domain long
<220> FEATURE:
<221> NAME/KEY: misc_feature
<222> LOCATION: (1)..(1)
<223> OTHER INFORMATION: Xaa can be any amino acid residue
<220> FEATURE:
<221> NAME/KEY: misc_feature
<222> LOCATION: (8)..(16)
<223> OTHER INFORMATION: Xaa can be any amino acid residue
<220> FEATURE:
<221> NAME/KEY: misc_feature
<222> LOCATION: (23)..(23)
<223> OTHER INFORMATION: Xaa can be any amino acid residue

<400> SEQUENCE: 35

```
Xaa Ser Arg Asn Leu Ile Asp Xaa Xaa Xaa Xaa Xaa Xaa Xaa Xaa Xaa
1               5                   10                  15

Ser Arg Asn Leu Ile Asp Xaa
            20
```

<210> SEQ ID NO 36
<211> LENGTH: 6
<212> TYPE: PRT
<213> ORGANISM: Artificial
<220> FEATURE:
<223> OTHER INFORMATION: ring part of targeting domain

<400> SEQUENCE: 36

```
Ser Arg Asn Leu Ile Asp
1               5
```

<210> SEQ ID NO 37
<211> LENGTH: 5
<212> TYPE: PRT
<213> ORGANISM: Artificial
<220> FEATURE:
<223> OTHER INFORMATION: linker short

<400> SEQUENCE: 37

```
Lys Gly Ser Gly Gly
1               5
```

<210> SEQ ID NO 38
<211> LENGTH: 7
<212> TYPE: PRT
<213> ORGANISM: Artificial
<220> FEATURE:
<223> OTHER INFORMATION: linker long

<400> SEQUENCE: 38

```
Lys Gly Ser Gly Ser Gly Gly
1               5
```

<210> SEQ ID NO 39
<211> LENGTH: 22
<212> TYPE: PRT
<213> ORGANISM: Artificial
<220> FEATURE:
<223> OTHER INFORMATION: targeting domain

<400> SEQUENCE: 39

```
Cys Ser Arg Asn Leu Ile Asp Cys Lys Gly Ser Gly Gly Cys Ser Arg
```

```
1               5                   10                  15

Asn Leu Ile Asp Cys Ser
            20


<210> SEQ ID NO 40
<211> LENGTH: 24
<212> TYPE: PRT
<213> ORGANISM: Artificial
<220> FEATURE:
<223> OTHER INFORMATION: targeting domain

<400> SEQUENCE: 40

Cys Ser Arg Asn Leu Ile Asp Cys Lys Gly Ser Gly Ser Gly Gly Cys
1               5                   10                  15

Ser Arg Asn Leu Ile Asp Cys Ser
            20


<210> SEQ ID NO 41
<211> LENGTH: 22
<212> TYPE: PRT
<213> ORGANISM: Artificial
<220> FEATURE:
<223> OTHER INFORMATION: targeting domain

<400> SEQUENCE: 41

Cys Ser Arg Asn Leu Ile Asp Cys Gly Gly Gly Asp Gly Gly Cys Ser
1               5                   10                  15

Arg Asn Leu Ile Asp Cys
            20


<210> SEQ ID NO 42
<211> LENGTH: 21
<212> TYPE: PRT
<213> ORGANISM: Artificial
<220> FEATURE:
<223> OTHER INFORMATION: targeting domain

<400> SEQUENCE: 42

Cys Ser Arg Asn Leu Ile Asp Cys Gly Gly Asp Gly Gly Cys Ser Arg
1               5                   10                  15

Asn Leu Ile Asp Cys
            20


<210> SEQ ID NO 43
<211> LENGTH: 21
<212> TYPE: PRT
<213> ORGANISM: Artificial
<220> FEATURE:
<223> OTHER INFORMATION: targeting domain

<400> SEQUENCE: 43

Cys Ser Arg Asn Leu Ile Asp Cys Gly Asp Asp Gly Gly Cys Ser Arg
1               5                   10                  15

Asn Leu Ile Asp Cys
            20


<210> SEQ ID NO 44
<211> LENGTH: 22
<212> TYPE: PRT
<213> ORGANISM: Artificial
<220> FEATURE:
<223> OTHER INFORMATION: targeting domain

<400> SEQUENCE: 44
```

-continued

```
Cys Ser Arg Asn Leu Ile Asp Cys Gly Gly Gly Gly Gly Gly Cys Ser
1               5                   10                  15

Arg Asn Leu Ile Asp Cys
            20


<210> SEQ ID NO 45
<211> LENGTH: 9
<212> TYPE: PRT
<213> ORGANISM: Artificial
<220> FEATURE:
<223> OTHER INFORMATION: PDGF receptor binding sequence
<220> FEATURE:
<221> NAME/KEY: MOD_RES
<222> LOCATION: (1)..(1)
<223> OTHER INFORMATION: Any amino acid available for cross-linking
<220> FEATURE:
<221> NAME/KEY: misc_feature
<222> LOCATION: (1)..(9)
<223> OTHER INFORMATION: Cross-link between residues
<220> FEATURE:
<221> NAME/KEY: MOD_RES
<222> LOCATION: (9)..(9)
<223> OTHER INFORMATION: Any amino acid available for cross-linking

<400> SEQUENCE: 45

Xaa Ser Arg Asn Leu Ile Asp Cys Xaa
1               5


<210> SEQ ID NO 46
<211> LENGTH: 8
<212> TYPE: PRT
<213> ORGANISM: Artificial
<220> FEATURE:
<223> OTHER INFORMATION: PDGF receptor binding sequence
<220> FEATURE:
<221> NAME/KEY: DISULFID
<222> LOCATION: (1)..(8)

<400> SEQUENCE: 46

Cys Ser Arg Asn Leu Ile Asp Cys
1               5


<210> SEQ ID NO 47
<211> LENGTH: 63
<212> TYPE: PRT
<213> ORGANISM: Artificial
<220> FEATURE:
<223> OTHER INFORMATION: IFN gamma analog

<400> SEQUENCE: 47

Cys Ser Arg Asn Leu Ile Asp Cys Lys Gly Ser Gly Gly Cys Ser Arg
1               5                   10                  15

Asn Leu Ile Asp Cys Ser Ala Ala Ala Ala Lys Phe Glu Val Asn Asn
            20                  25                  30

Pro Gln Val Gln Arg Gln Ala Phe Asn Glu Leu Ile Arg Val Val His
        35                  40                  45

Gln Leu Leu Pro Glu Ser Ser Leu Arg Lys Arg Lys Arg Ser Arg
    50                  55                  60


<210> SEQ ID NO 48
<211> LENGTH: 65
<212> TYPE: PRT
<213> ORGANISM: Artificial
<220> FEATURE:
<223> OTHER INFORMATION: IFN gamma analog

<400> SEQUENCE: 48
```

-continued

```
Cys Ser Arg Asn Leu Ile Asp Cys Lys Gly Ser Gly Ser Gly Gly Cys
1               5                   10                  15

Ser Arg Asn Leu Ile Asp Cys Ser Ala Ala Ala Ala Lys Phe Glu Val
            20                  25                  30

Asn Asn Pro Gln Val Gln Arg Gln Ala Phe Asn Glu Leu Ile Arg Val
        35                  40                  45

Val His Gln Leu Leu Pro Glu Ser Ser Leu Arg Lys Arg Lys Arg Ser
    50                  55                  60

Arg
65


<210> SEQ ID NO 49
<211> LENGTH: 117
<212> TYPE: DNA
<213> ORGANISM: Mus musculus
<220> FEATURE:
<221> NAME/KEY: CDS
<222> LOCATION: (1)..(114)

<400> SEQUENCE: 49

gcc aag ttt gag gtc aac aac cca cag gtc cag cgc caa gca ttc aat       48
Ala Lys Phe Glu Val Asn Asn Pro Gln Val Gln Arg Gln Ala Phe Asn
1               5                   10                  15

gag ctc atc cga gtg gtc cac cag ctg ttg ccg gaa tcc agc ctc agg       96
Glu Leu Ile Arg Val Val His Gln Leu Leu Pro Glu Ser Ser Leu Arg
            20                  25                  30

aag cgg aaa agg agt cgc tga                                          117
Lys Arg Lys Arg Ser Arg
        35


<210> SEQ ID NO 50
<211> LENGTH: 38
<212> TYPE: PRT
<213> ORGANISM: Mus musculus

<400> SEQUENCE: 50

Ala Lys Phe Glu Val Asn Asn Pro Gln Val Gln Arg Gln Ala Phe Asn
1               5                   10                  15

Glu Leu Ile Arg Val Val His Gln Leu Leu Pro Glu Ser Ser Leu Arg
            20                  25                  30

Lys Arg Lys Arg Ser Arg
        35


<210> SEQ ID NO 51
<211> LENGTH: 66
<212> TYPE: DNA
<213> ORGANISM: Artificial
<220> FEATURE:
<223> OTHER INFORMATION: BiPPB
<220> FEATURE:
<221> NAME/KEY: CDS
<222> LOCATION: (1)..(66)

<400> SEQUENCE: 51

tgt tct aga aac ctc atc gat tgt aag gga tcc gga ggt tgt tca cgt       48
Cys Ser Arg Asn Leu Ile Asp Cys Lys Gly Ser Gly Gly Cys Ser Arg
1               5                   10                  15

aat cta ata gat tgt tca                                               66
Asn Leu Ile Asp Cys Ser
            20


<210> SEQ ID NO 52
<211> LENGTH: 22
```

<212> TYPE: PRT
<213> ORGANISM: Artificial
<220> FEATURE:
<223> OTHER INFORMATION: Synthetic Construct

<400> SEQUENCE: 52

Cys Ser Arg Asn Leu Ile Asp Cys Lys Gly Ser Gly Gly Cys Ser Arg
1               5                   10                  15

Asn Leu Ile Asp Cys Ser
            20

<210> SEQ ID NO 53
<211> LENGTH: 126
<212> TYPE: DNA
<213> ORGANISM: Mus musculus

<400> SEQUENCE: 53
gcggccgcag ccaagtttga ggtcaacaac ccacaggtcc agcgccaagc attcaatgag     60
ctcatccgag tggtccacca gctgttgccg gaatccagcc tcaggaagcg gaaaaggagt    120
cgataa                                                               126

<210> SEQ ID NO 54
<211> LENGTH: 155
<212> TYPE: PRT
<213> ORGANISM: Mus musculus

<400> SEQUENCE: 54

Met Asn Ala Thr His Cys Ile Leu Ala Leu Gln Leu Phe Leu Met Ala
1               5                   10                  15

Val Ser Gly Cys Tyr Cys His Gly Thr Val Ile Glu Ser Leu Glu Ser
            20                  25                  30

Leu Asn Asn Tyr Phe Asn Ser Ser Gly Ile Asp Val Glu Glu Lys Ser
        35                  40                  45

Leu Phe Leu Asp Ile Trp Arg Asn Trp Gln Lys Asp Gly Asp Met Lys
    50                  55                  60

Ile Leu Gln Ser Gln Ile Ile Ser Phe Tyr Leu Arg Leu Phe Glu Val
65                  70                  75                  80

Leu Lys Asp Asn Gln Ala Ile Ser Asn Asn Ile Ser Val Ile Glu Ser
                85                  90                  95

His Leu Ile Thr Thr Phe Phe Ser Asn Ser Lys Ala Lys Lys Asp Ala
            100                 105                 110

Phe Met Ser Ile Ala Lys Phe Glu Val Asn Asn Pro Gln Val Gln Arg
        115                 120                 125

Gln Ala Phe Asn Glu Leu Ile Arg Val Val His Gln Leu Leu Pro Glu
    130                 135                 140

Ser Ser Leu Arg Lys Arg Lys Arg Ser Arg Cys
145                 150                 155

<210> SEQ ID NO 55
<211> LENGTH: 75
<212> TYPE: DNA
<213> ORGANISM: Artificial
<220> FEATURE:
<223> OTHER INFORMATION: BiPPB + linker

<400> SEQUENCE: 55
tgttctagaa acctcatcga ttgtaaggga tccggaggtt gttcacgtaa tctaatagat     60
tgttcagcgg ccgca                                                      75

<210> SEQ ID NO 56
<211> LENGTH: 180
<212> TYPE: PRT
<213> ORGANISM: Artificial
<220> FEATURE:
<223> OTHER INFORMATION: BiPPB-IFNgamma

<400> SEQUENCE: 56

```
Cys Ser Arg Asn Leu Ile Asp Cys Lys Gly Ser Gly Gly Cys Ser Arg
1               5                   10                  15

Asn Leu Ile Asp Cys Ser Ala Ala Ala Met Asn Ala Thr His Cys Ile
            20                  25                  30

Leu Ala Leu Gln Leu Phe Leu Met Ala Val Ser Gly Cys Tyr Cys His
        35                  40                  45

Gly Thr Val Ile Glu Ser Leu Glu Ser Leu Asn Asn Tyr Phe Asn Ser
    50                  55                  60

Ser Gly Ile Asp Val Glu Glu Lys Ser Leu Phe Leu Asp Ile Trp Arg
65                  70                  75                  80

Asn Trp Gln Lys Asp Gly Asp Met Lys Ile Leu Gln Ser Gln Ile Ile
                85                  90                  95

Ser Phe Tyr Leu Arg Leu Phe Glu Val Leu Lys Asp Asn Gln Ala Ile
            100                 105                 110

Ser Asn Asn Ile Ser Val Ile Glu Ser His Leu Ile Thr Thr Phe Phe
        115                 120                 125

Ser Asn Ser Lys Ala Lys Lys Asp Ala Phe Met Ser Ile Ala Lys Phe
    130                 135                 140

Glu Val Asn Asn Pro Gln Val Gln Arg Gln Ala Phe Asn Glu Leu Ile
145                 150                 155                 160

Arg Val Val His Gln Leu Leu Pro Glu Ser Ser Leu Arg Lys Arg Lys
                165                 170                 175

Arg Ser Arg Cys
            180
```

<210> SEQ ID NO 57
<211> LENGTH: 192
<212> TYPE: DNA
<213> ORGANISM: Artificial
<220> FEATURE:
<223> OTHER INFORMATION: BiPPB-IFNgamma mimetic
<220> FEATURE:
<221> NAME/KEY: CDS
<222> LOCATION: (1)..(192)

<400> SEQUENCE: 57

```
tgt tct aga aac ctc atc gat tgt aag gga tcc gga ggt tgt tca cgt       48
Cys Ser Arg Asn Leu Ile Asp Cys Lys Gly Ser Gly Gly Cys Ser Arg
1               5                   10                  15

aat cta ata gat tgt tca gcg gcc gca gcc aag ttt gag gtc aac aac       96
Asn Leu Ile Asp Cys Ser Ala Ala Ala Ala Lys Phe Glu Val Asn Asn
            20                  25                  30

cca cag gtc cag cgc caa gca ttc aat gag ctc atc cga gtg gtc cac      144
Pro Gln Val Gln Arg Gln Ala Phe Asn Glu Leu Ile Arg Val Val His
        35                  40                  45

cag ctg ttg ccg gaa tcc agc ctc agg aag cgg aaa agg agt cga taa      192
Gln Leu Leu Pro Glu Ser Ser Leu Arg Lys Arg Lys Arg Ser Arg
    50                  55                  60
```

<210> SEQ ID NO 58
<211> LENGTH: 63
<212> TYPE: PRT

```
<213> ORGANISM: Artificial
<220> FEATURE:
<223> OTHER INFORMATION: Synthetic Construct

<400> SEQUENCE: 58

Cys Ser Arg Asn Leu Ile Asp Cys Lys Gly Ser Gly Gly Cys Ser Arg
1               5                   10                  15

Asn Leu Ile Asp Cys Ser Ala Ala Ala Ala Lys Phe Glu Val Asn Asn
            20                  25                  30

Pro Gln Val Gln Arg Gln Ala Phe Asn Glu Leu Ile Arg Val Val His
        35                  40                  45

Gln Leu Leu Pro Glu Ser Ser Leu Arg Lys Arg Lys Arg Ser Arg
    50                  55                  60


<210> SEQ ID NO 59
<211> LENGTH: 22
<212> TYPE: PRT
<213> ORGANISM: Artificial
<220> FEATURE:
<223> OTHER INFORMATION: bicyclic peptide BiPPB
<220> FEATURE:
<221> NAME/KEY: DISULFID
<222> LOCATION: (1)..(8)
<220> FEATURE:
<221> NAME/KEY: DISULFID
<222> LOCATION: (15)..(22)

<400> SEQUENCE: 59

Cys Ser Arg Asn Leu Ile Asp Cys Gly Gly Gly Asp Gly Gly Cys Ser
1               5                   10                  15

Arg Asn Leu Ile Asp Cys
            20


<210> SEQ ID NO 60
<211> LENGTH: 22
<212> TYPE: PRT
<213> ORGANISM: Artificial
<220> FEATURE:
<223> OTHER INFORMATION: BiPPB for human stellate cells
<220> FEATURE:
<221> NAME/KEY: DISULFID
<222> LOCATION: (1)..(8)
<220> FEATURE:
<221> NAME/KEY: DISULFID
<222> LOCATION: (15)..(22)

<400> SEQUENCE: 60

Cys Ser Arg Asn Leu Ile Asp Cys Lys Gly Ser Gly Gly Gly Cys Ser
1               5                   10                  15

Arg Asn Leu Ile Asp Cys
            20


<210> SEQ ID NO 61
<211> LENGTH: 39
<212> TYPE: PRT
<213> ORGANISM: Artificial Sequence
<220> FEATURE:
<223> OTHER INFORMATION: signaling moiety consensus sequence
<220> FEATURE:
<221> NAME/KEY: MISC_FEATURE
<222> LOCATION: (1)..(4)
<223> OTHER INFORMATION: Xaa can be any amino acid residue
<220> FEATURE:
<221> NAME/KEY: MISC_FEATURE
<222> LOCATION: (6)..(6)
<223> OTHER INFORMATION: Xaa is a polar, uncharged residue such as Asn
      or Thr
<220> FEATURE:
```

<221> NAME/KEY: MISC_FEATURE
<222> LOCATION: (7)..(7)
<223> OTHER INFORMATION: Xaa can be any amino acid residue
<220> FEATURE:
<221> NAME/KEY: MISC_FEATURE
<222> LOCATION: (8)..(8)
<223> OTHER INFORMATION: Xaa is a non-polar, hydrophobic residue, such as Pro or Leu
<220> FEATURE:
<221> NAME/KEY: MISC_FEATURE
<222> LOCATION: (9)..(9)
<223> OTHER INFORMATION: Xaa is a polar, uncharged residue, such as Gln or Asn
<220> FEATURE:
<221> NAME/KEY: MISC_FEATURE
<222> LOCATION: (10)..(10)
<223> OTHER INFORMATION: Xaa is a non-polar, hydrophobic residue, such as Val, Ile or Leu
<220> FEATURE:
<221> NAME/KEY: MISC_FEATURE
<222> LOCATION: (12)..(12)
<223> OTHER INFORMATION: Xaa is a polar, basic residue, such as Arg, His or Lys
<220> FEATURE:
<221> NAME/KEY: MISC_FEATURE
<222> LOCATION: (13)..(13)
<223> OTHER INFORMATION: Xaa is any amino acid residue
<220> FEATURE:
<221> NAME/KEY: MISC_FEATURE
<222> LOCATION: (15)..(15)
<223> OTHER INFORMATION: Xaa is a non-polar, hydrophobic residue, such as Phe, Val or Ile
<220> FEATURE:
<221> NAME/KEY: MISC_FEATURE
<222> LOCATION: (16)..(16)
<223> OTHER INFORMATION: Xaa is any amino acid residue
<220> FEATURE:
<221> NAME/KEY: MISC_FEATURE
<222> LOCATION: (20)..(20)
<223> OTHER INFORMATION: Xaa is any amino acid residue
<220> FEATURE:
<221> NAME/KEY: MISC_FEATURE
<222> LOCATION: (22)..(22)
<223> OTHER INFORMATION: Xaa is a non-polar, hydrophobic residue, such as Val, Ile or Met
<220> FEATURE:
<221> NAME/KEY: MISC_FEATURE
<222> LOCATION: (23)..(24)
<223> OTHER INFORMATION: Xaa is any amino acid residue
<220> FEATURE:
<221> NAME/KEY: MISC_FEATURE
<222> LOCATION: (26)..(26)
<223> OTHER INFORMATION: Xaa is any amino acid residue
<220> FEATURE:
<221> NAME/KEY: MISC_FEATURE
<222> LOCATION: (28)..(32)
<223> OTHER INFORMATION: Xaa is any amino acid residue
<220> FEATURE:
<221> NAME/KEY: MISC_FEATURE
<222> LOCATION: (38)..(39)
<223> OTHER INFORMATION: Xaa is any amino acid residue

<400> SEQUENCE: 61

```
Xaa Xaa Xaa Xaa Val Xaa Xaa Xaa Xaa Xaa Gln Xaa Xaa Ala Xaa Xaa
1               5                   10                  15

Glu Leu Ile Xaa Val Xaa Xaa Xaa Leu Xaa Pro Xaa Xaa Xaa Xaa Xaa
            20                  25                  30

Lys Arg Lys Arg Ser Xaa Xaa
        35
```

<210> SEQ ID NO 62
<211> LENGTH: 9
<212> TYPE: PRT
<213> ORGANISM: Artificial Sequence
<220> FEATURE:

<223> OTHER INFORMATION: Targeting moiety

<400> SEQUENCE: 62

Cys Ser Arg Asn Leu Ile Asp Cys Ser
1 5

<210> SEQ ID NO 63
<211> LENGTH: 26
<212> TYPE: PRT
<213> ORGANISM: Artificial Sequence
<220> FEATURE:
<223> OTHER INFORMATION: targeting domain
<220> FEATURE:
<221> NAME/KEY: MISC_FEATURE
<222> LOCATION: (9)..(15)
<223> OTHER INFORMATION: any three of amino acids 9-15 can either be present or absent
<220> FEATURE:
<221> NAME/KEY: MISC_FEATURE
<222> LOCATION: (9)..(18)
<223> OTHER INFORMATION: maximum number of residues present is 7; minimum number of residues present is 4.
<220> FEATURE:
<221> NAME/KEY: MISC_FEATURE
<222> LOCATION: (16)..(18)
<223> OTHER INFORMATION: any one or all of amino acids 16-18 can either be present or absent

<400> SEQUENCE: 63

Cys Ser Arg Asn Leu Ile Asp Cys Gly Gly Gly Gly Gly Gly Gly Asp
1 5 10 15

Asp Asp Cys Ser Arg Asn Leu Ile Asp Cys
20 25

<210> SEQ ID NO 64
<211> LENGTH: 34
<212> TYPE: PRT
<213> ORGANISM: Artificial Sequence
<220> FEATURE:
<223> OTHER INFORMATION: nucelar transloxation consensus
<220> FEATURE:
<221> NAME/KEY: MISC_FEATURE
<222> LOCATION: (2)..(4)
<223> OTHER INFORMATION: Xaa can be any amino acid residue
<220> FEATURE:
<221> NAME/KEY: VARIANT
<222> LOCATION: (5)..(5)
<223> OTHER INFORMATION: Xaa is Gln or Asn
<220> FEATURE:
<221> NAME/KEY: VARIANT
<222> LOCATION: (6)..(6)
<223> OTHER INFORMATION: X is Phe, Val or Ile
<220> FEATURE:
<221> NAME/KEY: VARIANT
<222> LOCATION: (8)..(8)
<223> OTHER INFORMATION: Xaa is Arg or His
<220> FEATURE:
<221> NAME/KEY: VARIANT
<222> LOCATION: (9)..(9)
<223> OTHER INFORMATION: Xaa is Gln or Lys
<220> FEATURE:
<221> NAME/KEY: VARIANT
<222> LOCATION: (11)..(11)
<223> OTHER INFORMATION: Xaa is Phe, Val, or Ile
<220> FEATURE:
<221> NAME/KEY: VARIANT
<222> LOCATION: (12)..(12)
<223> OTHER INFORMATION: Xaa is Asn or His
<220> FEATURE:
<221> NAME/KEY: VARIANT
<222> LOCATION: (16)..(16)
<223> OTHER INFORMATION: Xaa is Arg or Gln
<220> FEATURE:
<221> NAME/KEY: MISC_FEATURE -continued
<222> LOCATION: (18)..(18)
<223> OTHER INFORMATION: Xaa is any amino acid residue
<220> FEATURE:
<221> NAME/KEY: VARIANT
<222> LOCATION: (19)..(19)
<223> OTHER INFORMATION: Xaa is His or Ala
<220> FEATURE:
<221> NAME/KEY: VARIANT
<222> LOCATION: (20)..(20)
<223> OTHER INFORMATION: Xaa is Gln or Asp
<220> FEATURE:
<221> NAME/KEY: VARIANT
<222> LOCATION: (22)..(22)
<223> OTHER INFORMATION: Xaa is Leu or Ser
<220> FEATURE:
<221> NAME/KEY: VARIANT
<222> LOCATION: (24)..(24)
<223> OTHER INFORMATION: Xaa is Asn or Ala
<220> FEATURE:
<221> NAME/KEY: VARIANT
<222> LOCATION: (25)..(25)
<223> OTHER INFORMATION: Xaa is Ser or Ala
<220> FEATURE:
<221> NAME/KEY: VARIANT
<222> LOCATION: (26)..(26)
<223> OTHER INFORMATION: Xaa is Ser or Ala
<220> FEATURE:
<221> NAME/KEY: VARIANT
<222> LOCATION: (27)..(27)
<223> OTHER INFORMATION: Xaa is Leu or Lys
<220> FEATURE:
<221> NAME/KEY: MISC_FEATURE
<222> LOCATION: (28)..(29)
<223> OTHER INFORMATION: Xaa is any amino acid residue

<400> SEQUENCE: 64

```
Val Xaa Xaa Xaa Xaa Xaa Gln Xaa Xaa Ala Xaa Xaa Glu Leu Ile Xaa
1               5                   10                  15

Val Xaa Xaa Xaa Leu Xaa Pro Xaa Xaa Xaa Xaa Xaa Xaa Lys Arg Lys
            20                  25                  30

Arg Ser
```

<210> SEQ ID NO 65
<211> LENGTH: 23
<212> TYPE: PRT
<213> ORGANISM: artificial
<220> FEATURE:
<223> OTHER INFORMATION: synthetic construct

<400> SEQUENCE: 65

```
Cys Ser Arg Asn Leu Ile Asp Cys Lys Gly Ser Gly Ser Gly Gly Cys
1               5                   10                  15

Ser Arg Asn Leu Ile Asp Cys
            20
```

<210> SEQ ID NO 66
<211> LENGTH: 72
<212> TYPE: DNA
<213> ORGANISM: artificial
<220> FEATURE:
<223> OTHER INFORMATION: synthetic construct

<400> SEQUENCE: 66

```
tgttcgcgga acctcatcga ttgtaaggga tccggaggtt gttcacgtaa tctaatagat     60

tgtgattgtt ta                                                         72
```

INTERFERON ANALOGS

The invention relates to the field of medicine. Among others, it relates to biologically active analogs of interferons (IFNs) which show less unwanted side-effects and to the therapeutic uses thereof.

About ten distinct IFNs have been identified in mammals; seven of these have been described for humans. They are typically divided among three IFN classes: Type I IFN, Type II IFN, and Type III IFN. All type I IFNs bind to a specific cell surface receptor complex known as the IFN-α receptor (IFNAR) that consists of IFNAR1 and IFNAR2 chains. The type I interferons present in humans are IFN-α, IFN-β and IFN-ω). Interferon type II binds to IFNGR. In humans this is IFN-γ. By interacting with their specific cell surface receptors, IFNs activate signal transducer and activator of transcription (STAT) complexes; STATs are a family of transcription factors that regulate the expression of certain immune system genes. Some STATs are activated by both type I and type II IFNs. However each IFN type can also activate unique STATs (Platanias, L. C. 2005 Nature reviews. Immunology 5 (5): 375-386).

IFNs belonging to all IFN classes are very important for fighting viral infections. Although they are named after their ability to "interfere" with viral replication within host cells, IFNs have other functions: they activate immune cells, such as natural killer cells and macrophages; they increase recognition of infection or tumor cells by up-regulating antigen presentation to T lymphocytes; and they increase the ability of uninfected host cells to resist new infection by virus. Certain host symptoms, such as aching muscles and fever, are related to the production of IFNs during infection.

IFNγ is a pleiotropic cytokine produced by the activated immune cells. It acts through the IFNγ receptor that is expressed nearly on all cell types, however it displays a strict species specificity. IFNγ has been applied for the treatment of immunological, viral and cancer diseases (Younes and Amsden, J Pharm Sci 2002) with significant effects. In addition, several studies have demonstrated the potential role of IFNγ in renal and liver fibrosis (Kidney Int. 1999; 56:2116-27, Hepatology 1996 23:1189-99).

Unfortunately, the short circulation half-life and undesirable systemic side effects of currently available interferons have limited its clinical application and even halted clinical trials. Many attempts have been made to circumvent these problems e.g. by incorporating $IFN_Y$ into liposomes, microspheres and elastomers (Pharm Res. 2000 17:42-8, Pharm Res. 1996 13:1464-75, J Control Release. 2005 102:607-17). Cell-specific delivery approaches have not been used so far. This is not surprising in view of the fact that such an approach is generally deemed impossible for cytokines which need to be delivered to their own receptors to elicit a biological effect, so that they always end up in target cells that express these receptors. Delivery to other target receptors will therefore in most cases be useless and at best lead to uptake in other cell types causing loss of activity or further diversification of adverse effects.

However, the present inventors recognized that the structure of INF offers unique targeting opportunities since the molecule contains a receptor binding moiety which is species-specific and a signaling moiety which is non-species specific and which acts intracellularly. It was surprisingly found that that the unique structure of $INF_Y$ allows delivery of the signaling moiety of $IFN_Y$ to another target receptor, provided that this new target receptor allows intracellular release of this signaling moiety and subsequent activation of the intracellular/nuclear $INF_Y$ signaling pathway. For example, a truncated IFNγ mimetic targeted to the Platelet Derived Growth Factor (PDGF) receptor displayed significantly less systemic side effects in an acute liver injury mouse model when compared to full length IFNγ or non-targeted IFNγ mimetic.

Accordingly, the invention relates to an analog of interferon (IFN), wherein the moiety mediating binding to its natural receptor is at least functionally disrupted and wherein the analog comprises a signaling moiety capable of mediating intracellular IFN activity, said signaling moiety being provided at its N-terminus, optionally via a linker, with at least one targeting domain capable of binding to a cell surface receptor other than the IFN receptor. Preferably, the analog is an IFN gamma (IFNγ) analog.

Interferon analogs provided with a heterologous targeting moiety are known in the art. WO2008/068621 discloses a conjugation product of IFNγ and a targeting moiety, such as a tumor targeting moiety or a tumor vasculature targeting moiety. The prior art only discloses conjugation to full length IFNγ, which will still bind to its native receptor causing adverse effects.

EP0844252 aims to provide cyclic peptides and their preparation process, which allow subsequent chemical grafting on coupling on said cyclic peptides, i.e. their attachment to a solid support, to a high molecular weight compound, to a marker and/or to other cyclic peptides, in order to provide new or improved biotechnological applications, particularly in the field of affinity chromatography, immunisation, development of diagnostic tests, vaccines and pharmaceutical compositions. It teaches the coupling of cyclic peptide ligands to biological molecules, among others to interferons. No mention is made in EP0844252 about the use of a truncated IFN molecule lacking a functional binding domain to its natural receptor.

An interferon analog of the present invention has clear and unexpected advantages over the use of a (modified) full length interferon, not only with respect to its therapeutic use (less side-effects, increased efficacy, reduced antigenicity because of lower molecular weight) but also to its production process (recombinant synthesis).

The functional disruption of the moiety mediating binding to its natural receptor can be achieved by deleting, inserting, substituting one or more relevant amino acid residues in the receptor binding domain. Interferon receptor binding domains have been identified and are known in the art. For example, binding of murine IFNγ to the INFγ receptor can be abolished by at least partially deleting the first 40, 30 or 20 N-terminal residues.

In one embodiment, the analog is a truncated IFNγ polypeptide which only contains the residues involved in intracellular signaling. As used herein, intracellular signaling may comprise nuclear translocation and/or anti-viral activity.

Preferably, the signaling moiety mediating intracellular activity comprises a polybasic nuclear localization signal (NLS) motif as found in the C-terminus of human and murine IFN (Subramaniam et al. 2000, J. Cell Science 113, 2771-2781). This NLS motif is thought to form a complex with a signal transducer and activator of transcription (STAT); STATs are a family of transcription factors that regulate the expression of certain immune system genes. Some STATs are activated by both type I and type II IFNs. However each IFN type can also activate unique STATs (Platanias, L. C. 2005 Nature reviews. Immunology 5 (5): 375-386) STAT activation initiates the most well defined cell signaling pathway for all IFNs, the classical Janus kinase-STAT (JAK-STAT) signaling pathway. In this pathway, JAKs associate with IFN receptors and, following receptor engagement with IFN, phosphorylate both STAT1 and STAT2. As a result, an IFN-stimulated gene factor 3 (ISGF3) complex forms—this contains STAT1, STAT2 and a third transcription factor called IRF9—and moves into the cell nucleus. Inside the nucleus, the ISGF3 complex binds to specific nucleotide sequences called IFN-stimulated response elements (ISREs) in the promoters of certain genes; this induces transcription of those genes.

An analog provided herein may comprise the polybasic NLS motif comprises the amino acid sequence (R)KRXRS (R), (SEQ ID NO: 1) wherein X is any amino acid residue, preferably wherein X is R, K, S or T. Preferably, the NLS motif is present at the C-terminal end of the analog. In one embodiment, it comprises the sequence, preferably the C-terminal sequence RKRKRSR (SEQ ID NO: 2), KSKRSR (SEQ ID NO: 3), KRTRS (SEQ ID NO: 4) or KRTRSQ (SEQ ID NO: 5).

In a specific aspect, the signaling moiety comprises or consists of a sequence selected from the group consisting of (a) the amino acid sequence KFEVNNPQVQRQAFNELIRVVHQLLPESSLRKRKRSR (SEQ ID NO: 6); (b) the amino acid sequence YSVTDLNVQRKAIHELIQVMAELSPAAKTGKRTRSQ (SEQ ID NO: 7) or YSVTDLNVQRKAIHELIQVMAELSPAAKTGKRKRSQ (SEQ ID NO: 8); (c) the amino acid sequence AKFEVNNPQIQHKAVNELIRVIHQLSPESSLRKRKRSRC (SEQ ID NO: 9)

(d) a stretch of at least 10, preferably at least 15, contiguous amino acids of the sequence of (a), (b) or (c);

Preferably, an analog of the invention comprises a stretch of at least 10, preferably at least 15, more preferably at least 20 contiguous amino acids of the sequence of (a) or (b) or (c). In one embodiment, said stretch comprises the N-terminal sequence of the sequence under (a) or (b) or (c). In another embodiment, it comprises the C-terminal sequence of the sequence under (a) or (b) or (c), preferably at least the last 15 amino acids. In yet another embodiment, the stretch comprises an internal sequence of the sequence under (a) or (b) or (c). Exemplary sequences are LLPESSLRKRKRSR, (SEQ ID NO: 13) KFEVNNPQVQRQ, (SEQ ID NO: 14) QAFNELIRVVHQLL, (SEQ ID NO: 15) MAELSPAAKTGKRTRSQ, (SEQ ID NO: 16), YSVTDLNVQRKAI, (SEQ ID NO: 17), KAIHELIQVMAELS (SEQ ID NO: 18).

The skilled person will understand that variants with one or more amino acid modifications to the sequences under (a) or (b) or (c) are also within the scope of the invention. the amino acid sequence under (a) or (b) or (c) wherein at most 10, preferably at most 8, more preferably at most 5 amino acid residues are deleted, added or substituted, provided that the signaling activity, for example nuclear translocation, is maintained.

Alignment of the human and murine INFγ sequences shows that 15 out of the 36 residues (41%) are identical and 24 out of the 36 residues (66%) are positively charged. The identity match is done according to clustal W alignment software.

```
                                                    (SEQ ID NO: 19)
huInterferon gamma 4 YSVTDLN VQR K AIHE L I Q V MAELS PAAKTG KRTRSQ 39
                      + V +   VQR + A +E L I + V + +L  P +    KR RS+
                                                    (SEQ ID NO: 20)
MuInterferon gamma 3 FEVNNPQ VQRQ  AFNE L I  RV VHQLL PESS LRKRK RS R 38
```

(e) an amino acid sequence showing at least 70%, preferably at least 80%, more preferably at least 90% identity to a) or b) or c) provided that the intracellular signaling activity is maintained; and (f) the amino acid sequence under (a) or (b) or (c) wherein at most 10, preferably at most 8, more preferably at most 5 amino acid residues are deleted, added or substituted, provided that the signaling activity, for example nuclear translocation, is maintained.

(g) the consensus sequence VxxxxVQRxAxxELIxVxxxLxPxxxxxKRxRS (SEQ ID NO: 10) wherein x is any amino acid residue;

The line in between the sequences indicates the conserved residues, yielding a consensus sequence recited under (g) herein above. Alignment of the human, rat and mouse interferon gamma can provide the consensus sequences under (h) and (i). In one embodiment, an analog comprises a signaling moiety according to the consensus sequence (g), (h) or (i) mentioned above. Other useful sequences include an amino acid sequences showing at least 70%, preferably at least 80%, more preferably at least 90%, most preferably at least 95% identity to (a) or (b) or (c) provided that the intracellular signaling activity is maintained.

In a specific aspect, the analog comprises a signalling moiety according to the consensus sequence:

(SEQ ID NO: 61)

$Xaa^1Xaa^2Xaa^3Xaa^4$ Val $Xaa^5$ $Xaa^6$ $Xaa^7$ $Xaa^8$ $Xaa^9$ Gln $Xaa^{10}$ $Xaa^{11}$ Ala $Xaa^{12}$ $Xaa^{13}$ Glu Leu Ile $Xaa^{14}$ Val $Xaa^{15}$ $Xaa^{16}$ $Xaa^{17}$ Leu $Xaa^{18}$ Pro $Xaa^{19}$ $Xaa^{20}$ $Xaa^{21}$ $Xaa^{22}$ $Xaa^{23}$Lys Arg Lys Arg Ser $Xaa^{24}$ $Xaa^{25}$, (h) the consensus sequence VxxxxxQxxAxxELIxVxxxLxPxxxxxKRKRS (SEQ ID NO: 11) wherein x is any amino acid residue;

(i) the consensus sequence Vxxxx[V/I]Q [R/H] [Q/K]A[F/V/I] [N/H]ELI[R/Q]Vx[H/A] [Q/E]L[L/S]P[E/A][S/A] [S/A] [L/K]xxKRKRS (SEQ ID NO: 12) wherein x is any amino acid residue;

The amino acid sequence under (a) represents a truncated murine INFy sequence, the sequence under (b) is a human homologue and the sequence under (c) is the rat homolog.

$Xaa^1$, $Xaa^2$, $Xaa^3$ $Xaa^4$ $Xaa^6$ $Xaa^{11}$, $Xaa^{13}$, $Xaa^{14}$, $Xaa^{16}$ $Xaa^{17}$, $Xaa^{18}$ $Xaa^{19}$ $Xaa^{20}$ $Xaa^{21}$ $Xaa^{22}$ $Xaa^{23}$ $Xaa^{24}$ and $Xaa^{25}$ is any amino acid residue $Xaa^5$ is a polar, uncharged residue such as Asn or Thr $Xaa^7$ is a non-polar, hydrophobic residue such as Pro or Leu $Xaa^8$ is a polar, uncharged residue such as Gln or Asn $Xaa^9$ is a non-polar hydrophobic residue such as Val, Ile or Leu $Xaa^{10}$ is a polar, basic residue such as Arg, His or Lys $Xaa^{12}$ is a non-polar hydrophobic residue such as Phe, Val or Ile $Xaa^{15}$ is a non-polar hydrophobic residue such as Val, Ile, Met Preferably, an analog comprises as signaling moiety a sequence corresponding to residues 95-133 in murine IFNγ or residues 95-134 in human IFNγ. This sequence has antiviral activity (Mujtaba et al. 2006, Clinical and Vaccine Immunology, Vol. 13, No. 8, p. 944-952).

The signaling activity of an analog can be readily determined by methods known in the art. For example, the capacity of the analog to induce nuclear translocation of STAT1α when taken up intracellularly by a murine macrophage cell line can be determined as described by Subramaniam et al. Signaling activity can also be assessed by complex formation with the transcription factor Stat1alpha and the nuclear importer of Stat1alpha, the importin-alpha analog NPI-1. See in particular Subramaniam et al. (2001, J. Interferon Cytokine Res. 21(11):951-959). Other suitable in vitro assays include NO-production in murine macrophages such as the RAW cell line. In one embodiment, the analog shows at least 30%, preferably at least 50%, more preferably at least 75% of the (in vitro) activity of its full length interferon counterpart. Cell specific targeting can significantly enhance the in vivo efficacy of an analog showing relatively low activity in vitro.

As mentioned herein above, an analog of the present invention is characterized by the absence of a functional IFN-receptor binding domain and the presence of a targeting domain capable of binding to an alternative receptor which can mediate intracellular uptake of the analog, for example a receptor which enters the endocytic pathway upon ligand binding and/or as part of constant receptor turn-over. As will be understood, the alternative or "secondary" receptor to be targeted should have some degree of cell type specific expression. Ubiquitously expressed receptors are less suitable candidates. Furthermore, the receptor must be expressed on a cell which is responsive to the intracellular signaling moiety, e.g. in case of an IFNγ analog it must contain an IFNγ-responsive element.

Preferably, the targeting domain can bind to a receptor that is specific for fibroblast and fibroblast-like cells, such as for example myofibroblasts, portal fibroblasts, mesangial cells, interstitial fibroblasts, alveolar fibroblasts or stromal cells. Also envisaged are receptors expressed on tumor cells. An IFNγ-analog can induce apoptosis in tumor cells, which can be specifically targeted via a secondary receptor expressed on tumor cells. In one embodiment, the receptor is selected from the group consisting of the PDGF receptors, collagen type VI receptor, cytokine receptors including TGF receptor, TNFα receptor and the IL1β receptor, Insulin growth factor receptors, VEGF receptors and chemokine receptors (e.g. CXCR4). Very good results were obtained when the analog was targeted to the PDGF receptor, preferably the PDGF-β receptor. Other suitable targeting domains include cell adhesion peptides, such as the tripeptide Arg-Gly-Asp (RGD) which was originally identified as the sequence within fibronectin that mediates cell attachment. The RGD motif has now been found in numerous other proteins and supports cell adhesion in many, but not all, of these. The integrins, a family of cell-surface proteins, act as receptors for cell adhesion molecules. A subset of the integrins recognize the RGD motif within their ligands, the binding of which mediates both cell-substratum and cell-cell interactions. RGD-containing analogs may be used as therapeutic agents for the treatment of diseases such as thrombosis and cancer.

In a specific aspect, the targeting domain targets can bind to a receptor for an oligosaccharide or a glycoprotein, preferably the asialoglycoprotein (ASGP) receptor or the mannose receptor (CD 206). For example, the targeting domain is an oligosaccharide, preferably mannose or lactose, conjugated to a carrier molecule. In another embodiment, mannose-6-phosphate (M6P) or a derivative thereof can be used as targeting domain for the M6P/IGF II receptor. See for example EP1117443.

The targeting domain is a preferably a proteinaceous substance (peptide) such that the analog as a whole is a fusion polypeptide which can be readily produced e.g. recombinantly. However, non-proteinaceous other types of targeting domains are also envisaged such as saccharides, lipids, nucleic acids, synthetic molecules, and the like.

In one aspect, the targeting domain comprises at least one cyclic peptide portion. Peptides can be cyclised by various means, including cysteine-disulfide or lanthionine bridge formation. Cyclic peptides useful for targeting an analog of the invention to a desired cell type are described in the art. For example, EP1117443 discloses a cyclic peptide comprising at least one sequence encoding a cell receptor recognising peptide (RPR). In one embodiment, an analog of the invention comprises in its (cyclised or linear) targeting domain at least an amino acid sequence selected from the group consisting of RGD, KPT, SRN, NLI and LID.

A preferred embodiment relates to analogs having a targeting domain which comprises multiple receptor binding sequences, preferably in the form of at least one tandem repeat of a (cyclic) peptide portion. The tandem repeat may comprise two cyclic peptide portions, preferably identical cyclic peptide portions, connected via a linker of 1 to 5 amino acids. This is of particular advantage for targeting a receptor which is active as a dimer, such as the PDGF, TGFβ or IL-10 receptor.

In one embodiment, the targeting domain comprises one, preferably two, copie(s) of the amino acid sequence $X_1$SRNLID$X_2$, (SEQ ID NO: 21) wherein $X_1$ and $X_2$ denote moieties which together can form a (peptidic) bond such that a cyclic structure is formed wherein the sequence SRNLID (SEQ ID NO: 36) is part of the ring. The two copies are preferably spaced by a linker sequence of 1 to 7 amino acids. Preferably, $X_1$ and $X_2$ are Cys residues. The inventors found that a targeting domain comprising the amino acid sequence CSRNLIDC(SEQ ID NO:46)-linker-CSRNLIDCS (SEQ ID NO: 62), wherein the linker is an amino acid sequence of 1 to 7, like 1, 2, 3, 4, 5, 6 or 7, amino acid residues, is very effective in binding to the dimeric PDGFβ receptor. For example, they performed a comparative experiment wherein two cyclic peptides capable of binding to the PDGF-receptor were linked to each other via a spacer consisting of 6 amino acids whereas in another construct these two cyclic peptides were coupled via a spacer of 11 amino acids. In both constructs the spacer contained a lysine residue to allow coupling of a drug or tracer. Both bicyclic constructs were labeled with FITC and added to 3T3 cell cultures, expressing the PDGF-receptor and incubated for 2 hrs to examine the binding. Following incubation and staining with an antibody against FITC, immunohistochemical data showed significant binding of the construct comprising the spacer of 6 amino acids, whereas only low binding was observed with the construct containing the longer spacer of 11 amino acids.

In one embodiment, the linker may consist of 4 or 5 amino acid residues, preferably selected from the group of Gly, Ala, Ser and Thr residues, more preferably at least 3 of them being a glycine residue. Preferred linkers consist of the sequences KGSGG (SEQ ID NO:37) and KGSGSGG (SEQ ID NO:38). As a specific example, the targeting domain comprises or consists of the amino acid sequence CSRNLIDCKGSGGC-SRNLIDCS (SEQ ID NO: 39), or CSRNLIDCKGSGSGGC- SRNLIDCS (SEQ ID NO: 40). In another embodiment, the linker consists of 5 or 6 amino acid residues, preferably selected from the group of Asp, Lys, Gly, Ala, Ser and Thr residues. Good results were obtained with a linker of 4 to 7 residues, at least 4, preferably at least 5, being a glycine residue. Other suitable linkers include a sequence of 4 to 7 residues, the residues being selected from Gly and Asp residues, e.g. [$G_n$ $D_m$] wherein n+m is from 4 to 7, wherein n≥4 and M an integer between 0 and 3. In a specific embodiment, the targeting domain comprises or consists of the amino acid sequence CSRNLIDC[GnD m]CSRNLIDC, (SEQ ID NO: 63), wherein n+m is from 4 to 7, wherein n≥4 and M an integer between 0 and 3. For example, the targeting domain consists of or comprises the sequence CSRNLIDCGGGDGGCSRNLIDC, (SEQ ID NO: 41), CSRNLIDCGGDGGCSRNLIDC, (SEQ ID NO: 42), CSRNLIDCGDDGGCSRNLIDC (SEQ ID NO: 43), or CSRNLIDCGGGGGGCSRNLIDC (SEQ ID NO: 44).

The targeting domain may be attached to the signalling domain by any means, for instance by a linker or spacer sequence. Suitable linker sequences are typically up to 15, preferably up to 10 amino acid residues in length. Polyalanine linkers may be used. For instance, provided herein is an interferon gamma analog, consisting of the sequence CSRNLIDCKGSGGCSRNLIDCSAAAAKFEVNNPQVQRQAFNELIRVVHQLLPESS LRKRKRSR, (SEQ ID NO: 30), CSRNLIDCKGSGSGGCSRNLIDCSAAAAKFEVNNPQVQRQAFNELIRVVHQLLPE SSLRKRKRSR (SEQ ID NO: 31), or CSRNLIDCGGGDGGCSRNLIDCSAAAKFEVNNPQVQRQAFNELIRVVHQLLPESS LRKRKRSR (SEQ ID NO: 32).

The targeting domain may also be attached to the signaling domain via a carrier molecule, e.g. albumin. This is especially advantageous if the targeting domain is a non-proteinaceous substance e.g. an oligosaccharide such as mannose or lactose. In one embodiment, the carrier molecule comprises free reactive groups like hydroxyl, amine and/or sulphate. The size of the carrier is preferably an endogenous plasma protein, like albumin, lactoferrin or fibronectin.

The invention also relates to a conjugate comprising a compound of interest, e.g. a biologically active molecule, conjugated to a bicyclic PDGF-targeting domain, said targeting domain comprising two copies of the amino acid sequence $X_1$SRNLID$X_2$, (SEQ ID NO: 21), wherein $X_1$ and $X_2$ denote moieties which together can form a bond, like a peptidic or disulphide bond, such that a bicyclic structure is formed wherein the sequence SRNLID (SEQ ID NO: 36), is part of each ring. Preferably, $X_1$ and $X_2$ are Cys residues allowing for cyclisation via disulphide bond formation. A conjugate according to the invention is characterized in that the two copies are spaced by a linker sequence of 2 to 7 amino acids. It was surprisingly found that this specific spacer length allows for highly efficient targeting of the PDGF receptor, which is active as a dimer. Thus, also provided is a conjugate comprising a compound of interest conjugated to a targeting domain, said targeting domain comprising the amino acid sequence $X_1$SRNLID$X_2$(SEQ ID NO:21)-linker-$X_3$SRNLID$X_4$, (SEQ ID NO: 21), wherein the pair of $X_1$ and $X_2$ and the pair of $X_3$ and $X_4$ can form a (peptidic) bond such that a bicyclic structure is formed wherein the sequences SRNLID (SEQ ID NO: 36), are part of a ring, and wherein the linker is an amino acid sequence consisting of 2 to 7 amino acid residues. As discussed herein above, the linker may consist of 4 or 5 amino acid residues. They can be selected from the group of Gly, Ala, Ser, Asp, Lys and Thr residues, preferably at least 3 of them being a glycine residue. Preferred linkers consist of the sequences KGSGG (SEQ ID NO: 37) and KGSGSGG (SEQ ID NO:38). As a specific example, the targeting domain comprises or consists of the amino acid sequence CSRNLIDCKGSGGCSRNLIDCS (SEQ ID NO: 39), or CSRNLIDCKGSGSGGCSRNLIDCS (SEQ ID NO: 40). In another embodiment, the linker consists of 5 or 6 amino acid residues, preferably selected from the group of Asp, Gly, Ala, Ser and Thr residues. Good results were obtained with a linker of 4 to 7 residues, at least 4, preferably at least 5, being a glycine residue. Other suitable linkers include a sequence of 4 to 7 residues, the residues being selected from Gly and Asp residues, e.g. [GnD m] wherein n+m is from 4 to 7, wherein n≥4 and M an integer between 0 and 3. In a specific embodiment, the targeting domain comprises or consists of the amino acid sequence CSRNLIDC [GnDm] CSRNLIDC, (SEQ ID NO: 63), wherein n+m is from 4 to 7, wherein n≥4 and M an integer between 0 and 3. For example, the targeting domain consists of or comprises the sequence CSRNLIDCGGGDGGCSRNLIDC, (SEQ ID NO: 41),
CSRNLIDCGGDGGCSRNLIDC, (SEQ ID NO: 42),
CSRNLIDCGDDGGCSRNLIDC (SEQ ID NO: 43), or
CSRNLIDCGGGGGGCSRNLIDC (SEQ ID NO: 44).

The use of the sequence SRNLID (SEQ ID NO: 36), as cell targeting domain is known in the art. W000/23113 discloses the conjugation of a cyclic peptide comprising a receptor recognizing peptide (RRP) to a carrier molecule being larger than 5000 Dalton, for instance serum albumin. An exemplary RRP is the PDGF receptor binding sequence XSRNLIDCX, (SEQ ID NO: 45), wherein X denotes the location of cyclisation. It is taught that, within the cyclic peptide structure, multiple RRP sequences may be present. It is also disclosed to attach more than one (e.g. 5-15 cyclic peptides) to a carrier molecule. Hagens et al. (2007) Pharmaceutical Res. Vol. 24, pp. 566-574, show the delivery of cyclic peptide CSRNLIDC (SEQ ID NO: 46), conjugated to albumin to hepatic stellate cells. Thus, the prior art conjugates all rely on attaching RRPs to a carrier molecule. The construction of conjugate of the invention, wherein the cyclic moieties are not attached to a carrier molecule but instead thereof placed in a tandem motif with a specific spacer length of 2 to 7 amino acids is not taught or suggested in the art. It was found that this well defined bicyclic structure enhances conjugate binding to the dimeric PDGF receptor as compared to a conjugate according to W000/23113, wherein the number and spatial orientation of the multiple receptor binding sequences attached to the carrier are randomized and much less controlled. The tandem configuration fixing the distance between the two cyclic moieties in a conjugate of the invention is designed to interact optimally with the dimeric PDGF-receptor. Furthermore, the presence of the relatively large carrier molecule may decrease receptor interactions by steric hindrance.

The bicyclic peptide can be prepared chemically or through recombinant techniques which provides production methods that are very favourable to the pharmaceutical industry. In addition, the bicyclic structure can be directly attached to a chemical entity (drug or tracer), polymer (eg Polyethylene glycol, PEG), small peptide or protein yielding a cell-specific low molecular weight compound that can easily penetrate into extravascular tissues. In particular for tumor targeting purposes, this tissue penetration may be very relevant.

Very good results were achieved with a linker consisting of 3 to 5 amino acid residues. In one embodiment, the conjugate comprises the amino acid sequence CSRNLIDC(SEQ ID NO:46)-linker-CSRNLIDCS(SEQ ID NO: 62), (BiPPB)

wherein the linker is an amino acid sequence of 2 to 7, preferably 3 to 5, amino acid residues. This bicyclic peptide is suitably used as low molecular weight targeting ligand with high affinity to the PDG F receptor (PDGF-R). The peptide can be prepared either by chemical or recombinant synthesis. The linker may comprise one or more amino acid residues with a reactive side chain that can be used for covalent attachment of a compound of interest, like a detectable label, a drug and/or diagnostic. Suitable reactive amino acids include lysine, serine and threonine, arginine, histidine, aspartic acid, glutamic acid, cysteine, asparagine, glutamine, tyrosine, methionine and tryptophan.

The biologically active moiety may have any type of useful biological activity, including cytokine, chemokine, or prostaglandin activity. It can be of proteinaceous or non-proteinaceous nature. For instance, the moiety is selected from the group selected from drugs, cytokines, chemokines, hormones, prostaglandins, and the like. Specific examples include PGE2, 15d-PGJ2, IL-10, IFNγ, truncated IFNγ. Proteinaceous moieties may conveniently be attached to the PDGF-R specific targeting domain by genetic fusion, at either the N- or C-terminus. In one embodiment, it is conjugated to the N-terminus.

An analog or conjugate according to the invention may be coupled to a core and/or carrier or delivery molecule by methods known in the art. Suitable cores or carriers include dendrimers, liposomes, and natural, synthetic or semi-synthetic polymers (branched or linear). Dendrimers have successfully proved themselves as useful additives in different routes of drug administration because they can render drugs greater water-solubility, bioavailability, and biocompatibility. See Chen et al., Journal of Pharmaceutical Sciences, Vol. 97 Issue 1, μg. 123-143. As an example, the invention provides an IFNγ-analog conjugated to a dendrimer or to a liposome. The liposome may contain (anti-cancer) drug.

In one embodiment, an interferon analog or PDGFR-targeted conjugate according to the invention is modified by conventional means to improve its pharmacological properties, like enhancing the efficacy and/or stability. In one embodiment, it is modified in order to enhance the half life by the attachment of at least one non antigenic polymer, for instance by a polymer selected from the group consisting of polyethylene glycols (PEGs) and derivatives thereof. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance.

A further aspect of the invention relates to an isolated nucleic acid sequence encoding a proteinaceous interferon analog according to the invention or encoding a proteinaceous PDGFR-targeted conjugate as described herein above. The skilled person will be able to design and construct a suitable nucleic acid sequence e.g. a fusion construct that encodes both the targeting moiety and the biologically active moiety using standard recombinant DNA technology. The isolated nucleic acid sequence may be part of an expression vector, for example a vector designed for recombinant protein production in a bacterial or mammalian host cell. Also provided is a host cell comprising a nucleic acid sequence or a vector according to the invention, preferably wherein said host cell is a bacterial or mammalian host cell. An analog or PDGF-targeted conjugate disclosed herein has improved properties with respect to its distribution within the body. More specifically, it allows directing a biologically active compound of interest to a cell of interest while maintaining the biological activity of that particular compound. To attain cell-specificity, these mediators are equipped with an address label that will increase their concentration around relevant target receptors in diseased tissue. A further embodiment therefore relates to a pharmaceutical composition comprising an IFN analog or a PDGF targeted conjugate and a pharmaceutically acceptable carrier. A specific aspect relates to a pharmaceutical composition comprising a targeted IFNγ analog, preferably a PDGF-targeted IFNγ analog showing reduced side-effects as compared to non-targeted IFNγ. An exemplary pharmaceutical composition contains a peptide comprising or consisting of the sequence CSRNLIDCKGSGGCSRNLIDCSAAAAKFEVNNPQ VQRQAFNELIRVVHQLLPESSLRKRKRSR (SEQ ID NO: 30), or CSRNLIDCKGSGSGGCSRNLIDCSAAAAKFEVNNPQVQRQAFNELIRVVH QLLPESSLRKRKRSR (SEQ ID NO: 31). Another exemplary pharmaceutical composition comprises a conjugate comprising a biologically active molecule conjugated to a targeting domain, said targeting domain comprising the amino acid sequence CSRNLIDC(SEQ ID NO:46)-linker-CSRNLIDCS, (SEQ ID NO: 62), wherein the linker is an amino acid sequence of 2 to 7, preferably 3 to 5, amino acid residues.

Also provided is the use of an IFN (γ) analog according to the invention for the manufacture of a medicament for the therapeutic or prophylactic treatment of a disease selected from cancer, viral diseases, fibrotic disease, sclerotic disease and chronic or acute inflammatory diseases. Exemplary diseases include glomerulosclerosis, interstitial fibrosis, lung fibrosis (idiopathic pulmonary fibrosis), atherosclerosis, rheumatoid arthritis, Crohns disease, colitis ulcerosa, glomerulonephritis and sepsis.

It is known that $INF_Y$ also has antiviral activity. Since the truncated form of $INF_Y$ is shown to be bioactive and found to display all activities of native $INF_Y$ provided a homing device is attached to the molecule, an analog of the invention is endowed with antiviral activity as well. Exemplary diseases included infections caused by influenza virus or human respiratory syncytial virus (RSV). RSV is a virus that causes respiratory tract infections. It is the major cause of lower respiratory tract infection and hospital visits during infancy and childhood. Sometimes an infant can become symptomatically infected more than once, even within a single RSV season. In the United States, 60% of infants are infected during their first RSV season, and nearly all children will have been infected with the virus by 2-3 years of age. Of those infected with RSV, 2-3% will develop bronchiolitis, necessitating hospitalization. Severe RSV infections have increasingly been found among elderly patients. There is no vaccine. Treatment is limited to supportive care, including oxygen. In temperate climates there is an annual epidemic during the winter months. In tropical climates, infection is most common during the rainy season.

The invention hence also relates to a method for therapeutic or prophylactic treatment of a disease selected from cancer, viral disease, fibrotic disease, sclerotic disease and chronic or acute inflammatory diseases such as glomerulosclerosis, interstitial fibrosis, lung fibrosis, atherosclerosis, rheumatoid arthritis, Crohns disease, colitis ulcerosa, glomerulonephritis and sepsis, comprising providing to a subject in need thereof a therapeutically effective dose of an IFN analog according to the invention. The disease may be a liver disease, preferably a chronic liver disease such as liver cirrhosis. The person skilled in the art will adjust the dosage to be applied to the manner of application, size, weight, state of health etc of the subject to which administration is to occur.

Administration can occur in any manner known per se for administration of a medicament. An IFNγ analog according to the invention is advantageously used in a medicinal composition (therapeutic or prophylactic) in a form for intrapulmonary delivery, e.g. by intranasal administration or inhalation. Also provided is an inhalation device comprising an IFNγ analog as active ingredient.

LEGEND TO THE FIGURES

FIG. 1: cloning of mimetic IFNγ from the mouse. Splenocytes were stimulated with PHA and RNA was isolated. RT and PCR using specific primers yielded a PCR product of the expected size. Expression of the construct in BL21 cells and Western blotting confirmed production of the mimetic.

Figure 2:
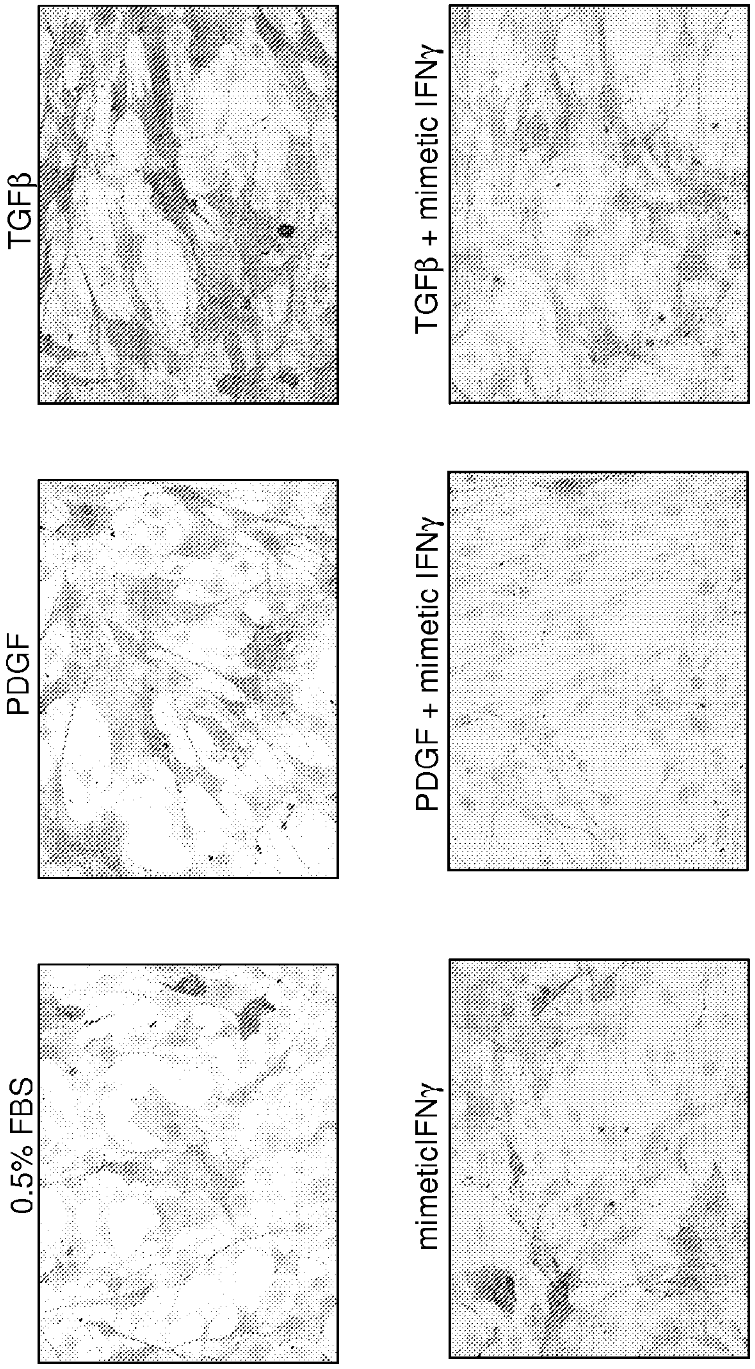

FIG. 2: Recombinant mimetic IFNγ shows anti-fibrotic effects in mouse 3T3 fibroblasts. Cells are stained for α-Smooth muscle actin which is a fibrosis marker.

Figure 3:
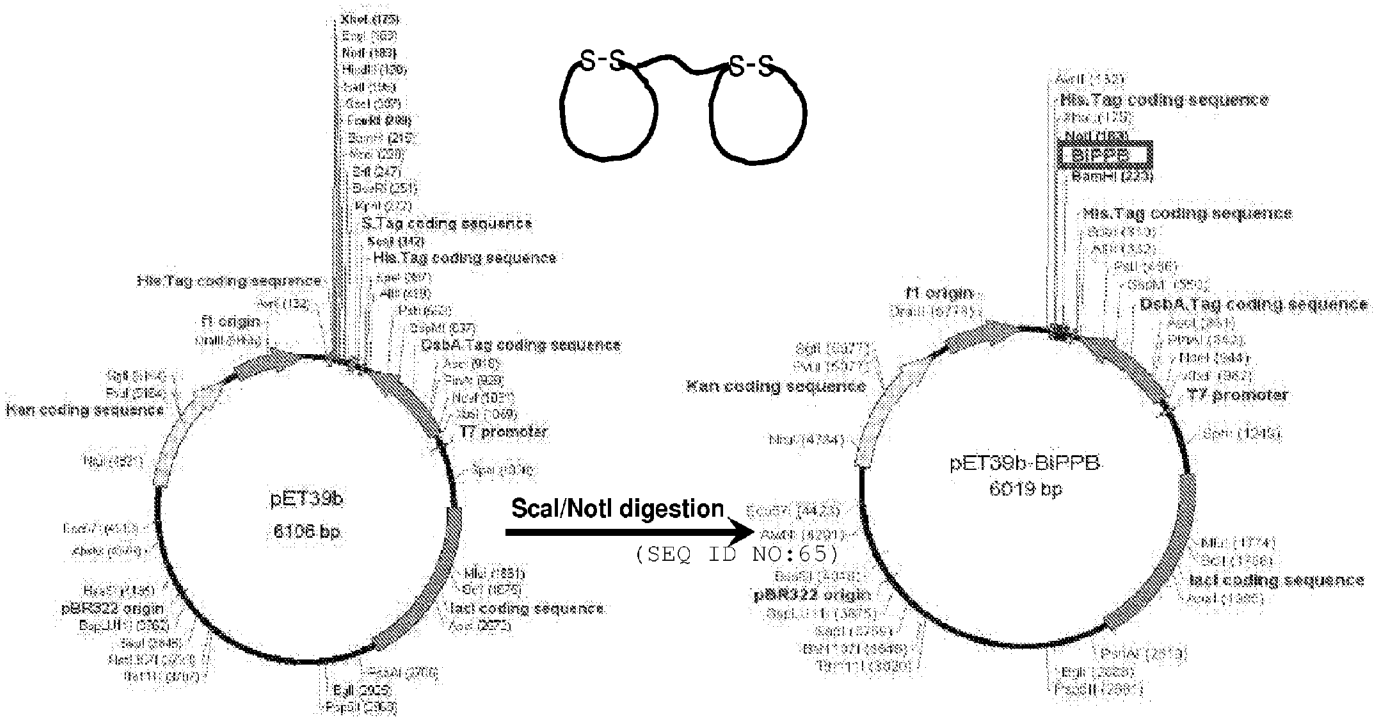

FIG. 3: Construction of pET39b-BiPPB encoding a bicyclic PDGF-receptor targeting domain.

Figure 4:
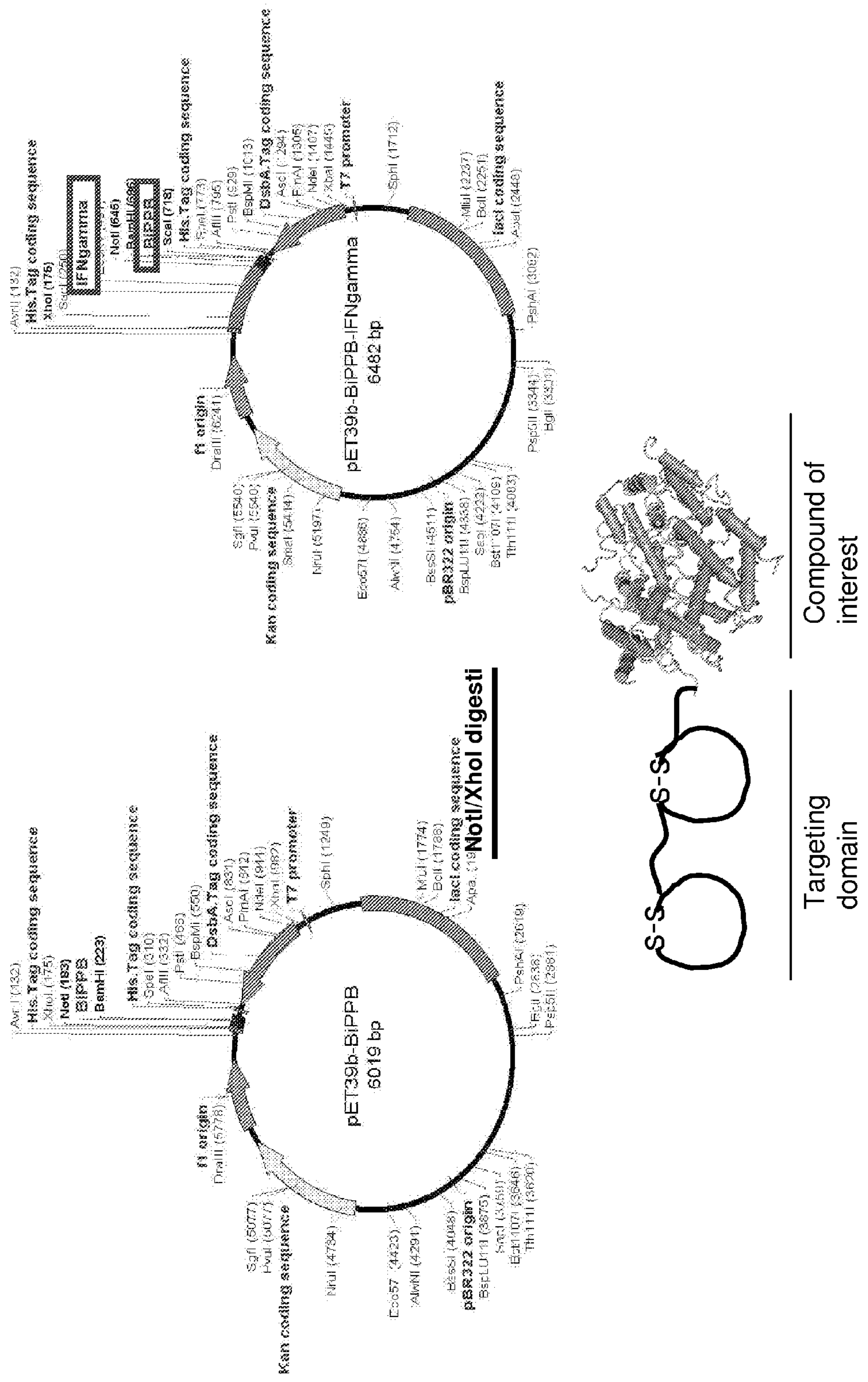

FIG. 4: Construction of pET39b-BiPPB-IFNgamma encoding a PDGFR-targeted IFNγ conjugate.

Figure 5:
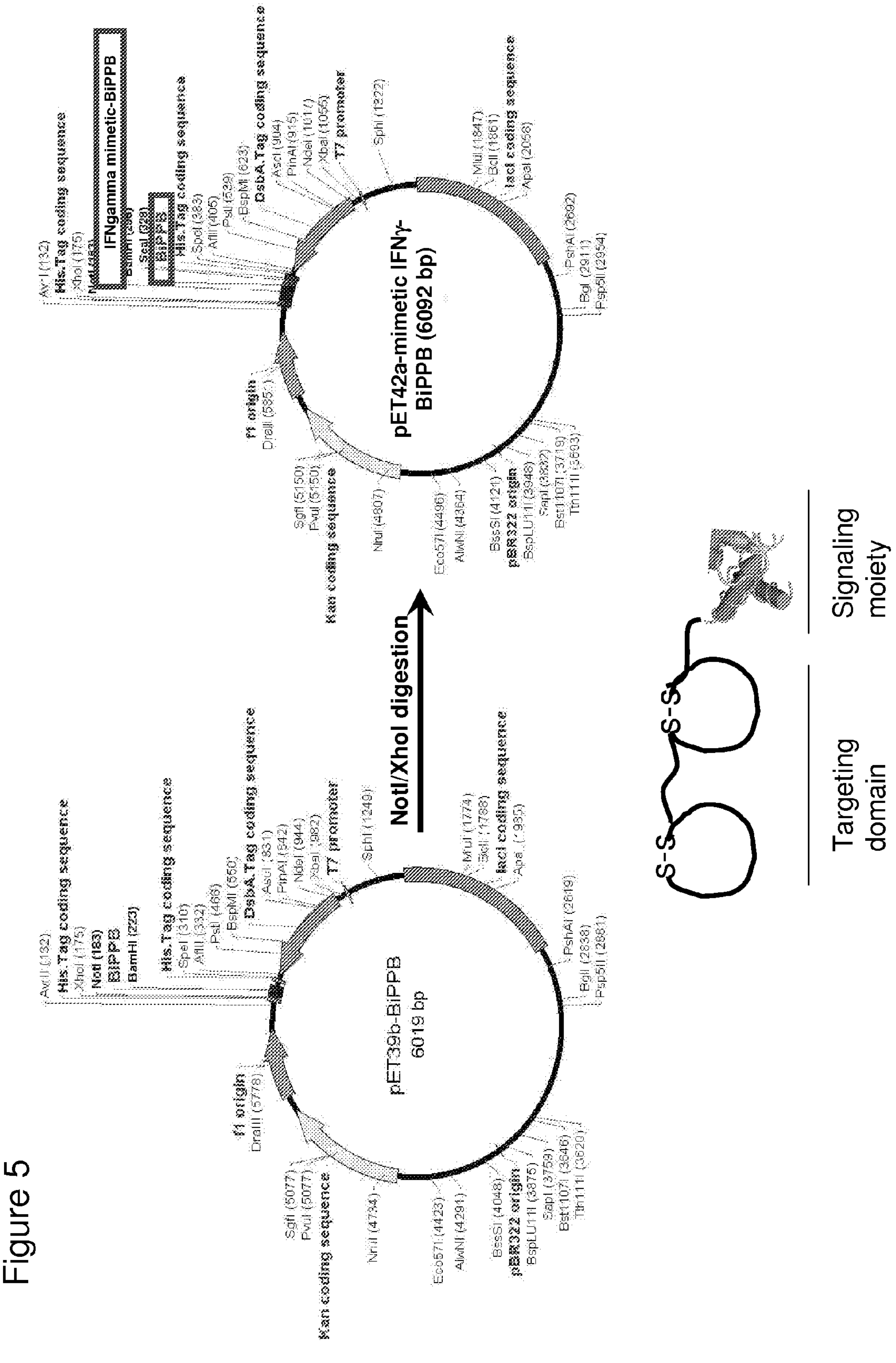

FIG. 5: Construction of pET39b-BiPPB-mimetic IFNγ.

Figure 6:
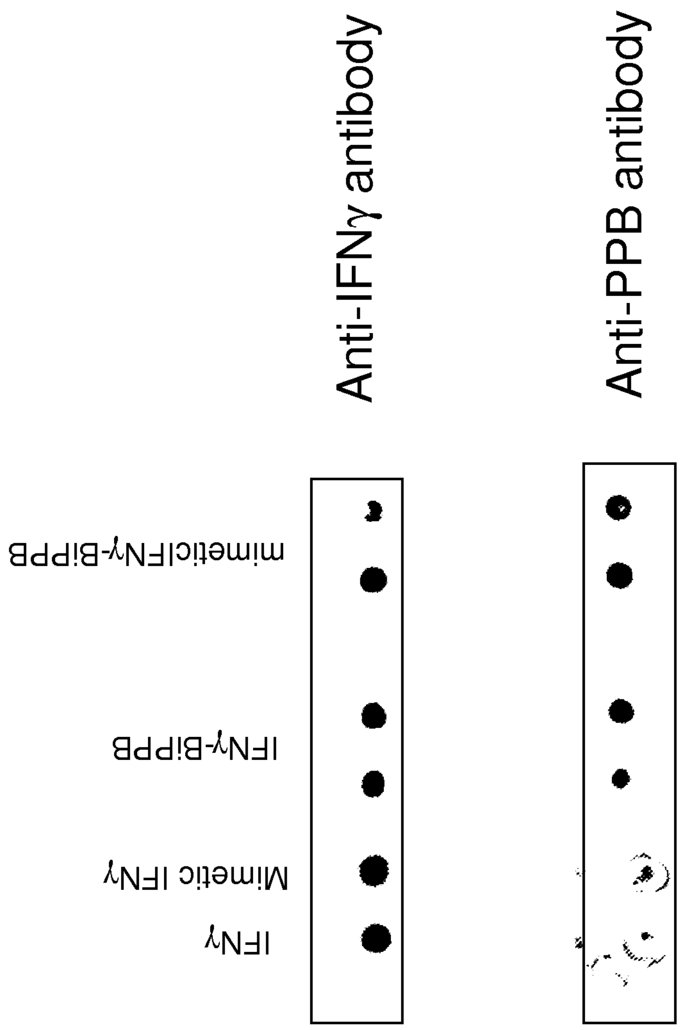

FIG. 6: Dot Blot analysis of IFNγ-BiPPB and Mimetic IFNγ-BiPPB showing the coupling of pPB-peptide to $INF_{Y}$.

Figure 7:
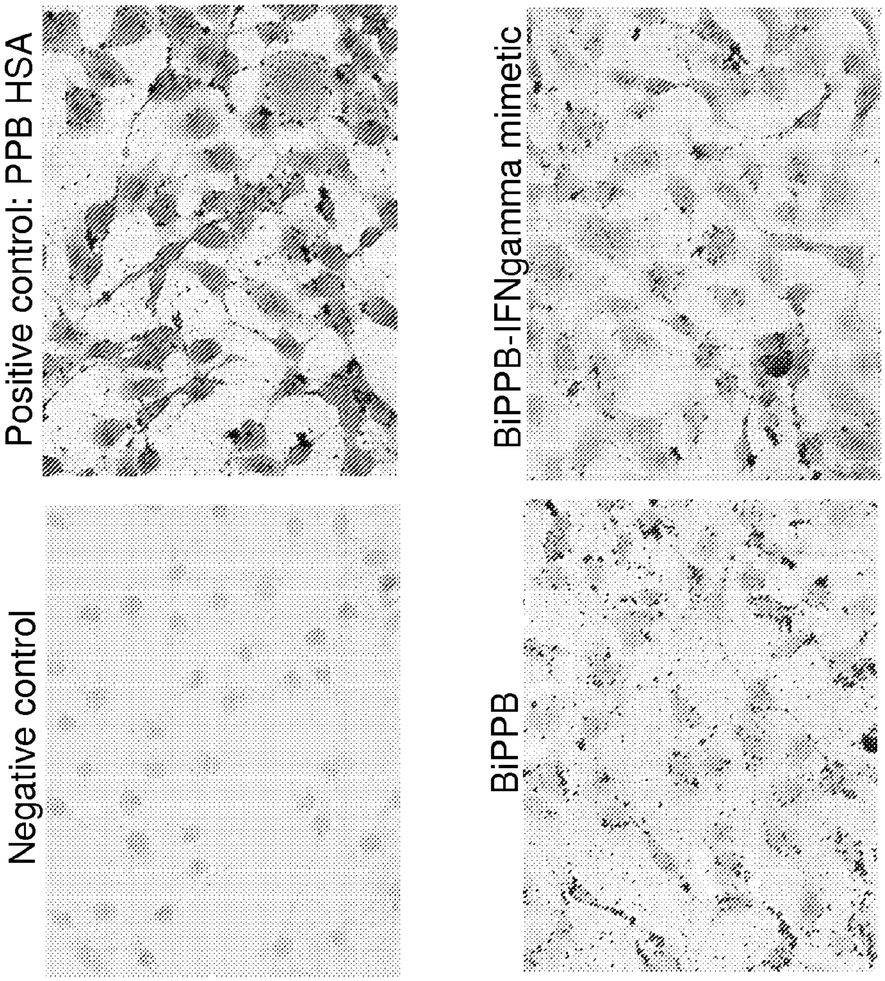

FIG. 7: Binding study in human hepatic stellate cell line LX2 cells. Cells were stained for PDGFR-binding peptide. Staining indicates the binding of pPB-containing constructs to the target cells.

Figure 8:
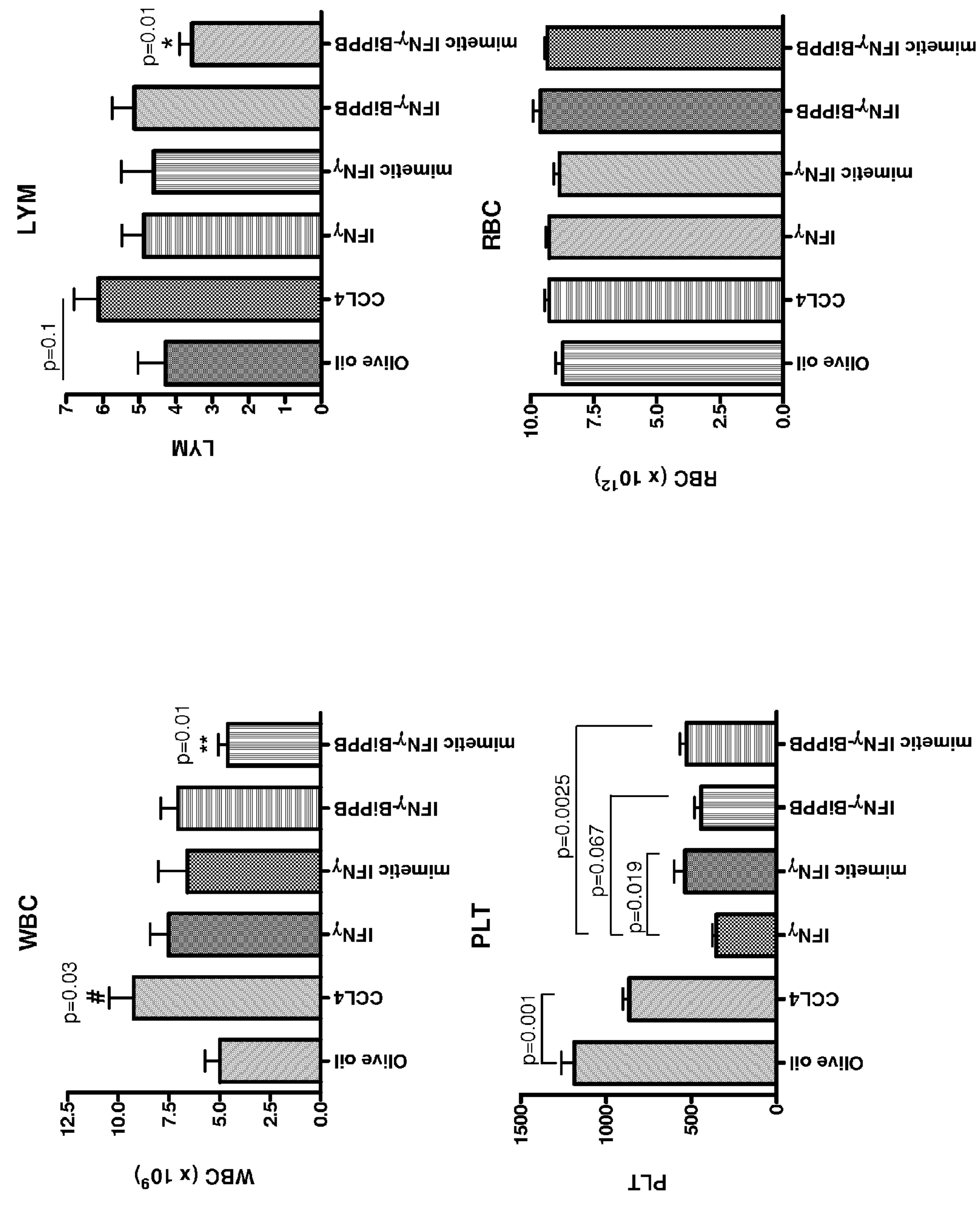

FIG. 8: Blood count analysis to study side effects of the treatment in acute liver injury mouse model. WBC=white blood cell count. LYM=lymphocytes. PLT=platelet count. RBC=red blood cell count. For details see Example 4.

Figure 9:
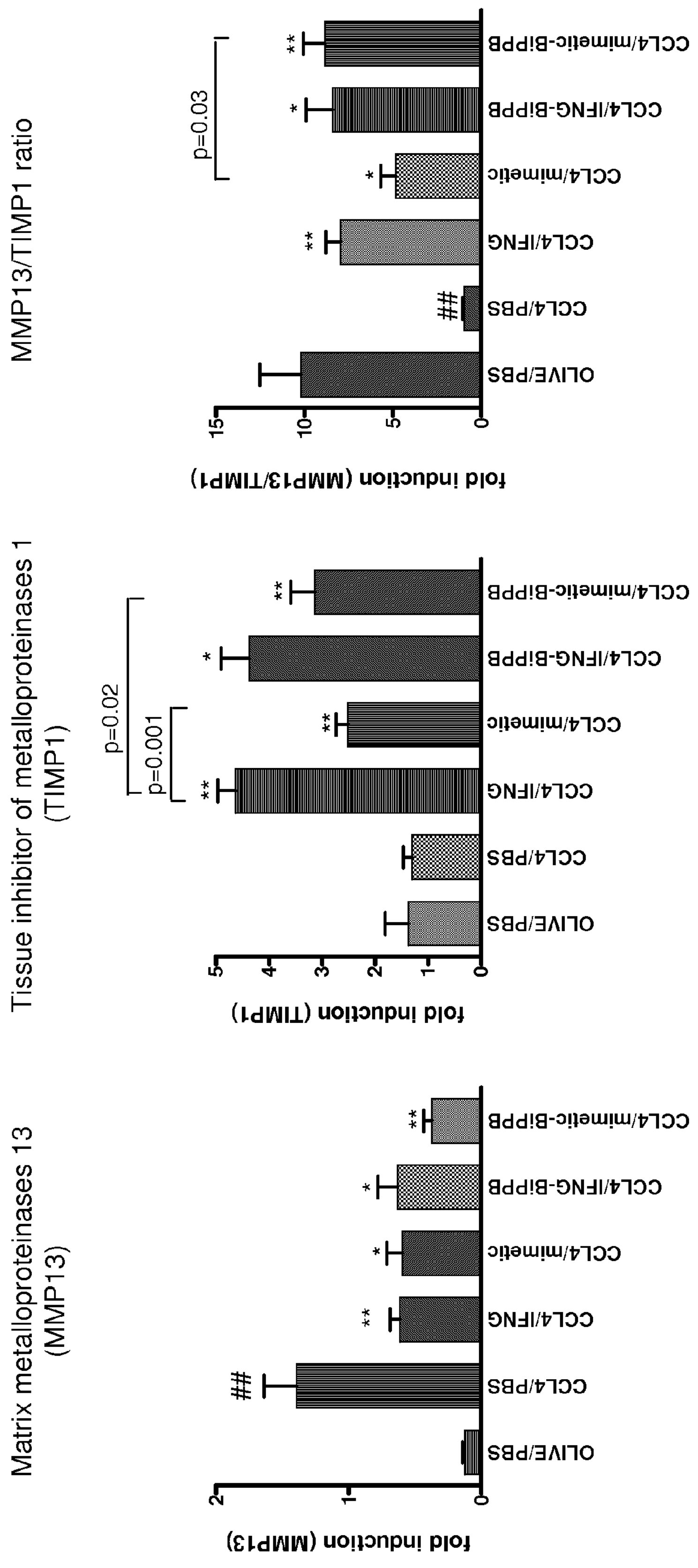

FIG. 9: Real Time PCR analysis of the liver fibrosis markers MMP13 and TIMP1. For details see Example 4.

Figure 10:
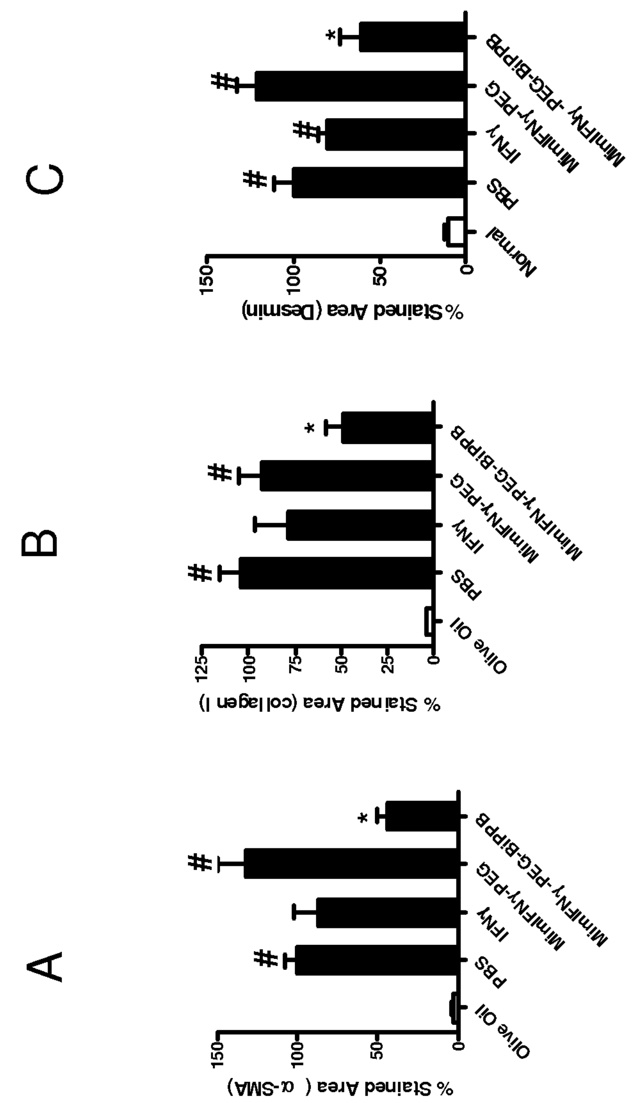

FIG. 10: Effect of mimetic IFNγ-PEG-BiPPB in the acute CCl4-induced liver-injury mouse model. Quantitation of a-SMA (A), collagen-I (B) and desmin (C)—staining of liver sections obtained from olive oil-treated normal mice and CCl4-treated mice receiving either IFNγ, mimetic IFNγ, mimetic IFNγ-PEG, mimetic IFNγ-PEG-BiPPB (5 μg/mice) or PBS alone. Quantitation was done using computerized Cell-D imaging software. Data represent the mean±SEM from 5 mice per group. #P<0.05 versus PBS-treated olive oil group; *P<0.05, **P<0.01 versus PBS treated-CCl4 group. For details see Example 6.

Figure 11:
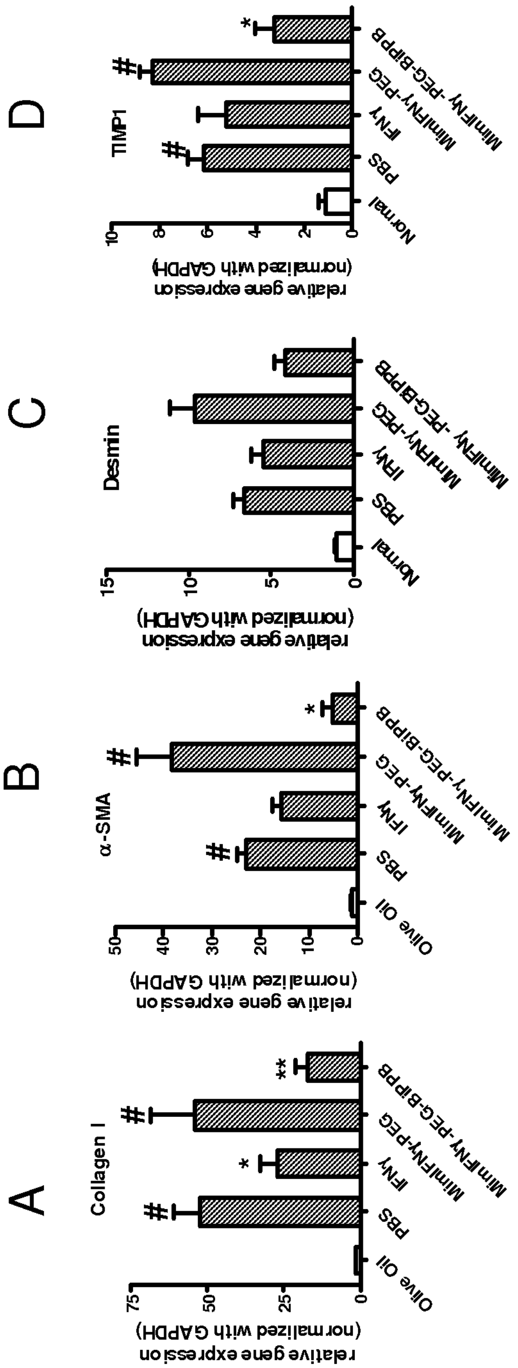

FIG. 11: Real Time PCR analysis of markers for liver fibrosis in mice, 3 days after CCl4 administration or olive oil. Mice were treated with different compounds as indicated and Collagen 1a1 (A), a-SMA (B), Desmin (C) and TIMP1 (D) mRNA levels were measured. For details see Example 6.

Figure 12:
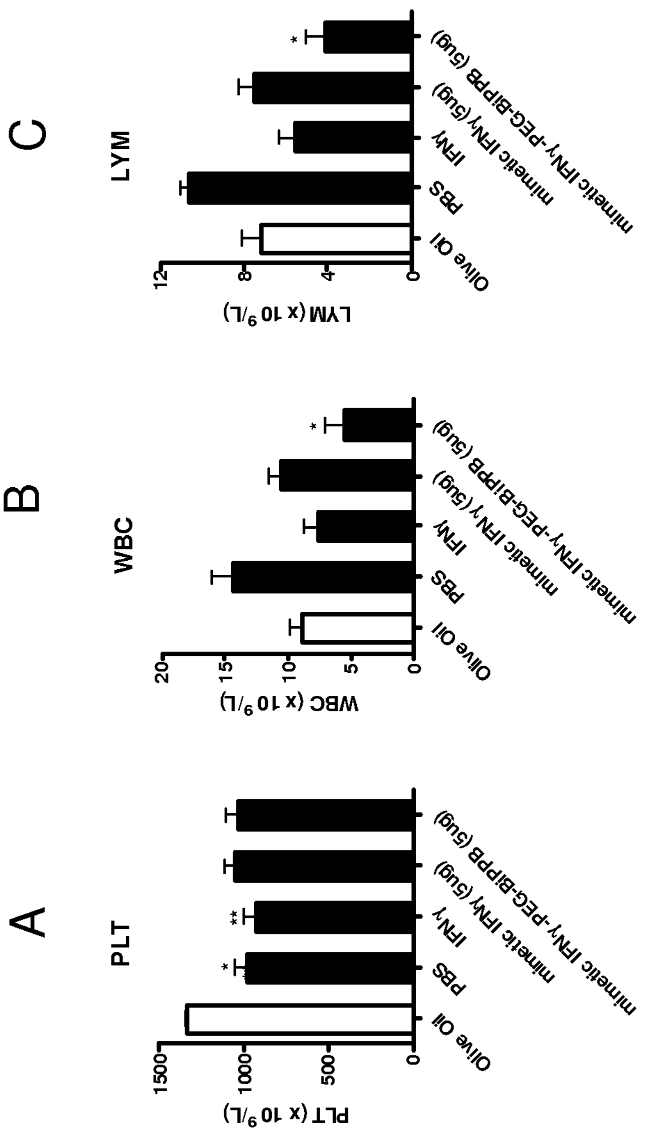

FIG. 12: Blood count analysis in whole blood of mice, 3 days after CCl4 administration or olive oil. Mice were treated with different compounds as indicated and Platelet count (PLT: fig A), white blood cell count (WBC, fig B) and lymphocyte count (C) were measured using a coulter counter. For details see Example 6.

EXPERIMENTAL SECTION

Liver Fibrosis is characterized by the excessive accumulation of the extracellular matrix components that leads to hepatic scars. To date, no successful therapy is available for the treatment of liver fibrosis. Hepatic stellate cells (HSCs) and fibroblasts are the key effector cells involved in the progression of the disease, which are activated by crucial growth factors like Platelet derived growth factor (PDGF) and transforming growth factor-beta (TGFβ). Interferon gamma (IFNγ) has been shown to have various beneficial effects in-vitro and in-vivo during liver fibrosis. However, IFNγ displays a strict species specificity and has a short circulating half life which limits its potential clinical use. Moreover, INFγ has serious adverse effects on the immune system, on endothelial cells and on the Central Nervous System (e.g. causing depressions) that all lead to frequent withdrawal of patients from clinical trials and consequently to failure of these trails. To circumvent these drawbacks, the present inventors produced a stable peptide mimetic of IFNγ that lacks the extracellular receptor recognition site and contains a signaling moiety which interacts directly at the downstream IFNγ signaling cascade, thereby retaining the prospective functions of IFNγ.

To increase the specificity of IFNγ and IFNγ mimetic peptide, IFNγ and mimetic peptide fused to BiPPB (Bicyclic peptide against the PDGF-beta-receptor) were been generated, since PDGF receptor expression is highly up-regulated during liver injury particularly in HSCs.

Example 1

Cloning of Mimetic IFNγ

Mouse splenocytes were isolated from fresh spleens and were cultured in the presence of PHA (Phytohemagglutinin) to stimulate cytokine production. After 24 hrs of stimulation, RNA was isolated and cDNA was synthesised using gene specific reverse primer followed by PCR amplification by phusion DNA polymerase using mimetic IFNγ specific forward and reverse primers. The obtained fragment was cloned in pET42a (prokaryotic expression vector) at PshA1/EcoRI site and the positive clones were checked by restriction digestion analysis. See FIG. 1.

The 5'→3' nucleotide sequence of the truncated mouse Interferon gamma (NCBI Reference sequence: NM_008337.2) (nt 457-nt 572) is as follows:

457 gcca agtttgaggt caacaaccca caggtccagc gccaagcatt caatgagctc atccgagtgg tccaccagct gttgccggaa tccagcctca ggaagcggaa aaggagtcgc tg 572 a (SEQ ID NO:49).

The last nucleotide has been added in order to insert the stop codon before cysteine, which is the last amino acid in the sequence. Cysteine is removed from the sequence to provide appropriate folding of the peptide and also to avoid inappropriate folding due to disulfide bonds in the fusion protein (with BiPPB).

The encoded amino acid sequence is

```
                                    (SEQ ID NO: 50)
AKFEVNNPQVQRQAFNELIRVVHQLLPESSLRKRKRSR*
*Denotes Stop codon
```

* Denotes Stop codon

Cloning of IFNγ-BiPPB and Mimetic IFNγ-BiPPB

A nucleic acid sequence encoding the bicyclic PDGF targeting domain BiPPB was generated by amplification of two fragments using 4 primers (2 for each fragment) and then ligated using inbuilt Bam HI restriction site and was then cloned in pET39b vector at ScaI/NotI site. IFNγ and Mimetic IFNγ was PCR amplified using peptide fusion primer (forward) and IFNγ or mimetic IFNγ reverse primer. The amplified fragment was digested and ligated in pET39b-BiPPB vector at NotI/XhoI site and the positive clones were checked by restriction digestion analysis. See FIGS. 4 and 5. The sequences of all the constructs were further confirmed by automated DNA sequencing.

BiPPB

Nucleotide sequence for BiPPB:
(SEQ ID NO: 51)
tgt tct aga aac ctc atc gat tgt aag gga tcc gga ggt tgt tca cgt aat cta ata gat tgt tca Amino acid sequence for BiPPB:
(SEQ ID NO: 52)
CSRNLIDCKGSGGCSRNLIDCS (see also FIG. 3)

Interferon Gamma (Full Length)

Nucleotide sequence: mouse Interferon gamma (NCBI Reference sequence: NM_008337.3)
(SEQ ID NO: 53)
gcggccgca 457 gcca agtttgaggt caacaaccca 481 caggtccagc gccaagcatt caatgagctc atccgagtgg tccaccagct gttgccggaa 541 tccagcctca ggaagcggaa aaggagtcg 569 ataa Amino acid sequence for Mouse IFNgamma
(SEQ ID NO: 54)
MNATHCILALQLFLMAVSGCYCHGTVIESLESLNNYFNSSGIDVEEKSLFLDIWRN

WQKDGDMKILQSQIISFYLRLFEVLKDNQAISNNISVIESHLITTFFSNSKAKKDAF

MSIAKFEVNNPQVQRQAFNELIRVVHQLLPESSLRKRKRSRC

Nucleotide sequence of the fused protein (BiPPB-IFN gamma)
(SEQ ID NO: 55)
tgt tct aga aac ctc atc gat tgt aag gga tcc gga ggt tgt tca cgt aat cta ata gat tgt tca gcggccgca Interferon gamma sequence (NM_008337.3).

Amino acid sequence for BiPPB-IFNgamma
(SEQ ID NO: 56)
*CSRNLIDCKGSGSGGCSRNLIDCS*AAAMNATHCILALQLFLMAVSGCYCHGTVIES

LESLNNYFNSSGIDVEEKSLFLDIWRNWQKDGDMKILQSQIISFYLRLFEVLKDNQ

AISNNISVIESHLITTFFSNSKAKKDAFMSIAKFEVNNPQVQRQAFNELIRVVHQLL

PESSLRKRKRSRC

Italics denotes BiPPB; normal text denotes IFNgamma mimetic; Bold denotes linker or spacer. See also FIG. 4.

Mimetic Interferon Gamma Fused to BiPPB

Nucleotide sequence of the fused protein (BiPPB-IFN gamma mimetic)
(SEQ ID NO: 57)
tgt tct aga aac ctc atc gat tgt aag gga tcc gga ggt tgt tca cgt aat cta ata gat tgt tca gcggccgca 457 gcca agtttgaggt caacaaccca caggtccagc gccaagcatt caatgagctc atccgagtgg tccaccagct gttgccggaa tccagcctca ggaagcggaa aaggagtcg 569 ataa Amino acid sequence for BiPPB-IFNgamma mimetic
(SEQ ID NO: 58)
*CSRNLIDCKGSGSGGCSRNLIDCS*AAA

AKFEVNNPQVQRQAFNELIRVVHQLLPESSLRKRKRSR*

Italics denotes BiPPB; normal text denotes IFNgamma mimetic; Bold denotes: linker or spacer. See also FIG. 5.

The nucleic acids were then transformed into BL21 cells (*E. coli*) for the expression using IPTG induction. The expressed protein was analysed by SDS-PAGE and Western blot analysis or Dot Blot analysis using anti-IFNγ antibody and/or anti-PPB antibody (see FIG. 6). The expressed protein (with His Tag) was then purified under native conditions through Ni-NTA column chromatography. The tags were proteolytically cleaved and further purified using sepharose column chromatography.

Example 2

Anti-Fibrotic Effects of Cleaved and Active Mimetic IFNγ

We evaluated the anti-fibrotic effects of cleaved IFNγ mimetic peptide in mouse NIH3T3 fibroblasts as assessed by immuno-cytochemistry (α-SMA staining). Briefly, 3T3 fibroblasts were seeded in 24 well plates at the density of $6\times10^4$ cells/well, After 24 hrs, cells were starved in 0.5% FBS containing medium for overnight. Thereafter, cells were incubated in starvation medium with different compounds (PDGF 50 ng/ml, TGFβ 10 ng/ml, mimetic IFNγ 1 μg/ml, 50 ng/ml PDGF+1 μg/ml mimetic IFNγ and 10 ng/ml TGFβ+1 μg/ml mimetic IFNγ). After 48 hrs of incubation, cells were washed, fixed with ethanol:acetone (1:1) and stained for α-SMA (marker of activated fibroblasts).

Example 3

Binding Study of BiPPB and Mimetic IFNγ-BiPPB in Human $LX_2$ Cells

We determined the binding of BiPPB and mimetic-BiPPB in $LX_2$ cells (human HSCs). Briefly, $LX_2$ cells were plated in 48 well plates at the cell density of $3\times10^4$ cells/well. After 24 hrs, cells were starved in medium (-FBS) for overnight. Then, cells were incubated with different compounds (BiPPB, PPB-HSA and BiPPB-Mimetic IFNγ) for 2 hrs at room temperature for binding. After binding, cells were extensively washed with PBS, fixed with ethanol:acetone (1:1) and stained for PPB. Results are presented in FIG. 7.

Example 4

In-Vivo Effect Study in Acute $CCl_4$-Induced Liver Injury in Mice

Recombinant IFNγ, mimetic IFNγ, recombinant fusion protein IFNγ-BiPPB and recombinant fusion protein mimetic IFNγ-BiPPB were tested for anti-fibrotic effects in acute $CCL_4$-induced liver injury mouse model. At day 1, the animals were given a single intra-peritoneal dose (1 ml/kg) of carbon tetrachloride ($CCl_4$) in olive oil or olive oil (controls n=6). After 24 hrs of $CCl_4$ injection, at day 2 and 3, animals were treated either with PBS (n=6), 50,000 U/mice of IFNγ (n=6), 50,000 U/mice of mimetic IFNγ (n=5), 50,000 U/mice of IFNγ-BiPPB (n=6), 50,000 U/mice of Mimetic IFNγ-BiPPB (n=6). Thereafter, at day 4, animals were sacrificed and blood counts were performed and anti-fibrotic effects (See Hemmann S, Graf J, Roderfeld M, Roeb. J Hepatol. 2007 May; 46(5):955-75) were evaluated using quantitative PCR. Results are presented in FIGS. 8 and 9.

The data presented in FIG. 8. demonstrate that mimetic-BiPPB is more effective than unmodified $INF_\gamma$ in attenuating the upregulation of white blood cell count (WBC) and lymphocyte count (lym) in whole blood associated with $CCl_4$-induced liver fibrosis ($p<0.01$). In contrast, the reduction in platelet count (PLT) associated with $INF_\gamma$ treatment (which is a well known adverse effect of $INF_\gamma$) is less severe when animals receive mimetic-$INF_\gamma$-BiPPB instead of unmodified $INF_\gamma$ ($p<0.0025$).

The data presented in FIG. 9 show that mimetic-$INF_\gamma$-BiPPB is endowed with antifibrotic activity: it attenuates $CCl_4$-induced upregulation of matrix metalloproteinases (MMP13). The ratio MMP-13 versus Tissue Inhibitor of Metalloproteinases (TIPM1) is similar to that obtained with native $INF_\gamma$, but better than mimetic $INF_\gamma$ ($p<0.03$), indicating that coupling of Bi-PPB to mimetic $INF_\gamma$ is beneficial. Collectively the data in FIGS. 8 and 9 show that mimetic $INF_\gamma$-BiPPB is more potent compared to native $INF_\gamma$ and has less side effects.

Example 5

Chemical Synthesis of Mimetic Interferon Gamma Conjugates

Mimetic IFNγ-PEG-BiPPB Conjugate:

0.111 μmol Bicyclic PDGFR recognizing peptide (BiPPB, 2223.2 Da, Genosphere Biotechnologies) was coupled with 0.337 μmol maleimide-PEG-succinimidyl carboxy methyl ester (Mal-PEG-SCM, 2 KDa, Creative PEGworks) for 3 hrs. Thereafter, lysine (0.337 μmol) was added to block free groups of Mal-PEG-SCM. After 1 hr of reaction, the synthesized product BiPPB-PEG-MAL (0.112 μmol) was reacted with 0.56 μmol of Mimetic IFNγ-ATA (4689 Da, Genosphere Biotechnologies) in the presence of deacetylating reagent for overnight at room temperature. Finally, the synthesized Mimetic IFNγ-PEG-BiPPB conjugate (8828.2 Da) was extensively dialyzed against PBS using 7 KDa slide-a-lyzer G2 dialysis cassettes (Thermo scientific).

Mimetic IFNγ-PEG Conjugate:

0.107 μmol Mimetic IFNγ-ATA (4689 Da) was reacted with 0.321 μmol of Poly(ethylene glycol)-succinimidyl α-methylbutanoate (mPEG-SMB, 2 KDa, Nektar therapeutics) for 2 hrs and subsequently the product was dialyzed extensively.

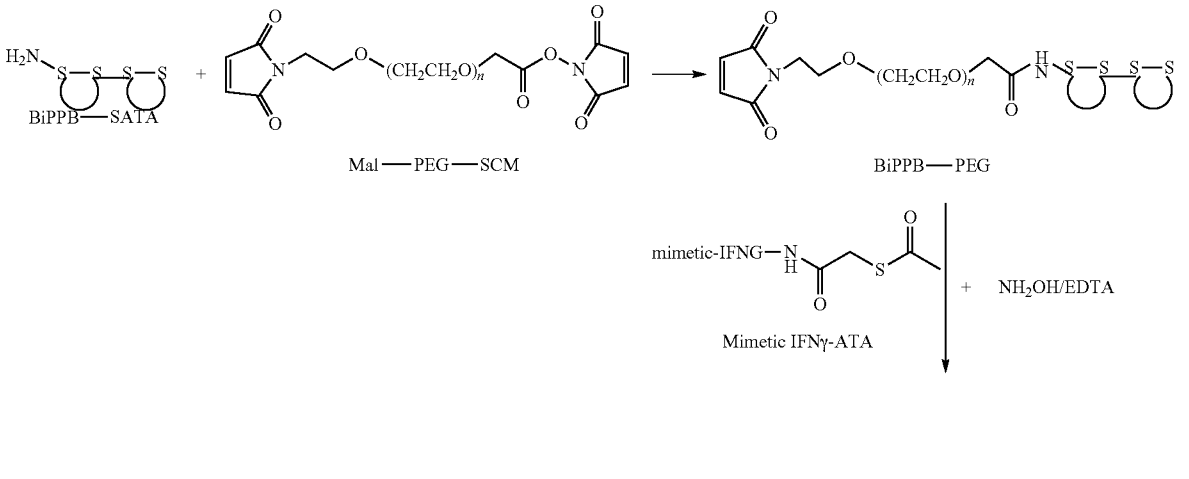

-continued

NH2—CSRNLIDCGGGDGGCSRNLIDC—COOH (SEQ ID NO: 41)

Bicyclic peptide

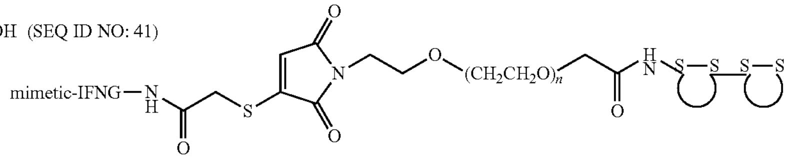

Mimetic IFNγ-PEG—BiPPB

Example 6

Effect on Fibrotic Parameters after Intravenous Administration of mimeticIFNγ-PEG-BiPPB in Acute Liver Injury Mouse Model Analysis of Fibrotic Parameters at the Protein Level:

Mice were intraperitoneally injected with $CCl_4$ at day 1 to induce liver injury. At day 2 and 3, mice were treated with IFNγ (5 ug/dose), mimetic IFNγ-PEG, mimetic IFNγ-PEG-BiPPB (5 μg/dose) or PBS alone. At day 4, animals were sacrificed; livers and different organs were collected for further analysis. Liver-sections were fixed with acetone, dried and rehydrated with PBS. Then, the sections were incubated with primary antibody (collagen, SMA and Desmin) for 1 hr. Thereafter, the sections were blocked with 0.03% $H_2O_2$ for endogenous peroxidase activity for 30 min. Subsequently, sections were incubated with secondary antibody HRP conjugated rabbit anti-goat antibody (1:100, DAKO) followed by HRP conjugated goat anti-rabbit antibody (1:100, DAKO) for 30 min. The peroxidase activity was developed using AEC (Sigma) for 20 min and nuclei were counterstained with hematoxylin (Fluka). The sections were mounted with Kaiser's gelatin and visualized under the light microscope (Olympus). For quantitative analysis, 27 microscopic pictures were captured and positively-stained areas were quantified using computerized Olympus Cell D imaging software. Results are shown in FIG. 10

Analysis of Fibrotic Parameters at the Gene Expression Level:

Total RNA from liver tissues was isolated using RNeasy mini kit (Qiagen) according to the manufacturer's instructions. The RNA concentration was quantitated by a UV spectrophotometer (NanoDrop Technologies, Wilmington, Del.). Total RNA (1.6 μg) were used for reverse transcription in total volume of 50 μl with the cDNA synthesis kit (Promega). All primers were purchased from Sigma-Genosys (Haverhill, UK). 10 ng of cDNA was used for quantitative real time PCR analysis. The reactions were performed using SYBR green PCR mix (Applied Biosystems) according to manufacturer's instructions. The samples were analyzed by ABI 7900HT sequence detection system (Applied Biosystems). Finally, the threshold cycle numbers (Ct) were calculated for each gene and relative gene expression was calculated after normalizing for expression of the reference gene GAPDH. Results are shown in FIG. 11. Analysis of adverse effects is depicted in FIG. 12.

Example 7

Effect on Fibrotic Parameters after Intravenous Administration of mimeticIFNγ-PEG-BiPPB in Established Advanced Liver Fibrosis Mouse Model Analysis of Fibrotic Parameters at the Protein Level:

Male balb/c mice (20-22 g) were treated with olive oil or increasing doses of $CCl_4$ (week 1: 0.5 ml/kg; week 2: 0.8 ml/kg and week 3-8: 1 ml/kg prepared in olive oil) twice weekly by intra-peritoneal injections for 8 weeks. In week 7 and 8, mice were treated intravenously with PBS, mimetic-IFNγ-PEG or MimeticIFNγ-PEG-BiPPB (5 μg/mice, thrice per week). All mice were sacrificed at week 8; blood and liver samples were collected for subsequent measurements. The liver sections were stained for Collagen I and desmin, CD68, 33D1 and MHC class II. It was found that the targeted truncated form of IFNγ (mimIFNγ-biPPB) induced substantial reduction in the fibrotic parameters in this chronic liver fibrosis model in mice; both collagen I and desmin staining was profoundly reduced in mimIFNγ-biPPB-treated $CCl_4$ mice compared to untreated $CCl_4$-mice. In contrast, treatment with untargeted mimIFNγ, lacking the receptor binding site, induced no effect on these parameters while full length mouse IFNγ induced only a small reduction in collagen I and desmin staining. The native (mouse) IFNγ induced infiltration of inflammatory cells ($CD68^+$ macrophages, neutrophils, $33D1^+$ dendritic cells) as well as increased MHCII expression. In contrast, MimIFNγ-BiPPB did not induce this increased inflammatory response in livers.

Example 8

Truncated IFNγ Analog Targeted to the PDGF Receptor is Active but Causes Less Side Effects A targeted conjugate of BiPPB chemically coupled mimetic-IFNγ was synthesized and characterized using Western blot analyses and for its anti-fibrotic effects in vitro in mouse 3T3 fibroblasts. In vivo, the targeted conjugate was examined in 4 days (acute) and 8 weeks (chronic) liver fibrosis models induced with $CCl_4$ in mice. Several fibrotic parameters and infiltration of inflammatory cells were assessed in the livers using immunohistochemistry and gene expression analysis.

Results:

The successfully synthesized conjugate caused inhibition of collagen expression in TGFbeta-induced mouse fibroblasts. In vivo, the targeted peptidomimetic of IFNγ (mimIFNγ-biPPB) induced substantial reduction in the fibrotic parameters in both acute and chronic liver fibrosis models in mice. Treatment with untargeted mimIFNγ, which lacks a receptor binding domain, showed no effect and unmodified mouse full length IFNγ showed only a moderate reduction. This mouse full length IFNγ induced infiltration of inflammatory cells ($CD68^+$ macrophages, neutrophils, $33D1^+$ dendritic cells) as well as increased MHCII expression. In contrast, MimIFNγ-BiPPB did not induce an inflammatory response (data not shown).

Example 9

Study with MimeticIFNγ-PEG-BiPPB in Subcutaneous Tumor Model in Mice

Materials and Methods

Normal male C57BL/6 and Balb/c mice weighing 20 to 25 g were obtained from Harlan (Zeist, the Netherlands). They were kept at a 12:12-hour light/dark cycle and received ad libitum normal diet. All experimental protocols for animal studies were approved by the Animal Ethics Committee of the University of Groningen. To induce subcutaneous tumors, C26 cells were cultured in 125-$mm^3$ flasks a day before injection in animals to keep them in the growth phase. Cells were detached by trypsanization, and trypsin was removed by centrifugation. The cell pellet was resuspended in PBS. A total of $1\times10^6$ cells (B16 and C26 cells) suspended in 100 μl of PBS were injected subcutaneously in the flank of Balb/c mice. Tumor growth was followed by measuring tumor size using a digital Vernier caliper. Tumor volume was established using the formula: a×b2/2, where a denotes tumor length and b denotes the tumor width. C26 tumors were induced in mice as described. The treatment was started on day 5 when the tumor volume was reached the range of 50 to 100 $mm^3$ because this tumor size has been shown as an optimum tumor size for the start of the treatment. Animals (n=4 per group) were injected intravenously with six doses of either vehicle (PBS), mimeticIFNγ-PEG (5 μg/dose), mimeticIFNγ-PEG-BiPPB (5 μg/dose) on alternative days under anesthesia ($O_2$/isoflurane). Tumor size was measured under anesthesia. The animals with C26 tumors were killed on day 20 because no effect of the treatment was observed. Animals were killed under gas anesthesia ($O_2$/isoflurane), and tumors were isolated and fixed in cold isopentane for cryosections.

4-μm-thick cryostat sections were prepared from snap-frozen tissue and stained for CD31 according to standard immunoperoxidase methods. We analyzed CD31 staining (endothelial cell marker) for the determination of the blood vessel lumen area and blood vessel density in tumor sections of C26 tumors. Results showed significant angiogenesis in untreated tumors and in tumors of mice treated with mimetic IFNγ, while mice treated with mimetic IFNγ-BiPPB displayed a strong reduction in angiogenesis in their tumors (data not shown).

Example 10

Effect of PDGF-Receptor Targeted Truncated $INF_Y$ on Pulmonary Fibrosis

Background and Rationale for $INF_Y$-Based Therapies in IPF Patients:

Idiopathic pulmonary fibrosis (IPF) is a progressive parenchymal lung disease with a median survival of only 3-5 years following diagnosis[1, 2]. Besides IPF also other types of lung fibrosis have a poor prognosis, in particular fibrosing non-specific interstitial pneumonia (NSIP) and end-stage fibrosis of for example several auto-immune diseases and extrinsic allergic alveolitis. There are currently no effective therapies for lung fibrosis due to poor understanding of the disease mechanisms.

The (myo)fibroblast has a central role in all types of lung fibrosis[3]. Ongoing damage to the lungs leads to initiation of dysregulated repair mechanisms with recruitment of fibroblasts and their transformation to myofibroblasts. Myofibroblasts are the key effector cells in fibrosis producing excessive amounts of extracellular matrix components like collagens. Myofibroblasts are currently thought to be the most important therapeutic target for treatment of lung fibrosis[3]. Key growth factors in the proliferation and transformation of myofibroblasts are transforming growth factor beta (TGFβ), platelet-derived growth factor (PDGF), and endothelin-1 and many new therapies have focused on inhibiting these factors or their receptors. However, most of the clinical trials based on modulating myofibroblast behaviour have shown disappointing results.

Interferon gamma (IFNγ) is probably the most-studied anti-fibrotic mediator in clinical trials of IPF. It mediates myofibroblast growth arrest and apoptosis through a STAT-1 (Signal Transducers and Activators of Transcription-1)-dependent pathway, which is important for resolution of fibrogenic responses[4]. Despite an initial promising start, the large INSPIRE trial concluded that IFNγ did not prolong survival[5]. IFNγ, however, was administered subcutaneously and since IFNγ receptors are found on almost all cells in the body, it has severe dose-limiting side effects. These include influenza-like illness and fatique[5]. Inhaled administration can partly circumvent this problem and one trial is currently registered to study the effects of aerosolized IFNγ in IPF.

Another way to increase the concentration of IFNγ within myofibroblasts, and thus the efficacy, is to use the concept of drug targeting: drugs are coupled to cell-selective drug carriers that are specifically taken up by target cells, the drugs are released within those cells thereby reducing systemic side effects while attaining high local concentrations in target cells. Myofibroblasts for instance specifically upregulate PDGF-receptors that can be used for drug targeting purposes[6].

Although $CCl_4$ induces liver fibrosis, the lungs also have low expression of Cytochrome P450 activity and $CCL_4$ (turned into toxic compounds by this enzyme) is therefore also slightly activated in lung tissue. These leads to activation of profibrotic cells which in turn express the PDGF receptor, which initiates profibrotic activity. This model has been used to as a model of idiopathic pulmonary fibrosis (IPF, see ref 8 and 9). While exploring the antifibrotic effects of $INF_Y$ in liver tissue, a significant change in lung tissue was noted by the examiners. The weight of lungs from $CCl_4$-treated mice was significantly higher than lungs of normal mice (0.75±0.05% of body weight in normal versus 2.03±0.15% of b.w. in untreated $CCl_4$-treated mice; P<0.01) yet this increase was significantly reduced by treatment with PPB-PEG-$INF_Y$ (1.53±0.11% of b.w.; P<0.05 vs untreated $CCl_4$ mice). Microscopical examination revealed that the lungs of $CCl_4$-treated mice were affected by diffuse alveolitis, a condition which can precede fibrosis, and lungs displayed an enhanced collagen staining. When these mice were treated with IFNγ coupled to PDGF-receptor recognizing peptides, we found a significantly reduced alveolitis in lungs and a reduced collagen deposition. Of note, these beneficiary effects of targeted IFNγ were attained after establishing the lung disease.

We therefore conclude that PDGF-receptor-targeted $INF_Y$ is able to accumulate in any tissue with significant PDGFβ-receptor expression, and is able to exert an antifibrotic effect in other tissues as well as illustrated by its effect in lungs. The $INF_Y$ analogs of the invention may thus be used for the treatment of idiopathic fibrosis and other forms of fibrosis or sclerosis in other tissues characterized by enhanced expression of the PDGF-receptor.

Example 11

Targeting of Truncated IFN Gamma to Various Receptors

In this experiment it is shown that an analog of the invention comprising the signaling moiety of murine IFNγ (mimiFNγ) and a cell surface targeting domain can be efficiently targeted not only to the PDGF receptor but also to other cell surface receptors. Exemplary targeting domains tested include lactose (ligand for the Asialoglycoprotein (ASGP)), mannose (ligand for the mannose receptor (CD 206) and the tripeptide RGD (ligand for the receptor avβ3 integrin receptor). The sequence of 30 mimiFNγ consisted of FEVNNPQVQRQAFNELIRVVHQLLPESSLRKRKRSR(SEQ ID NO: 36). Various cell types and different parameters for testing IFNγ activity used in the study. The control samples were exposed to intact murine INNγ. For details see the Table below.

| IFNγ analog | Target receptor | Cells used | Parameter measured (details see text) | Results |
|---|---|---|---|---|
| Lactose-HSA-PEG-mimIFNγ | Asialoglycoprotein (ASGP) receptor | Human Hepatocytes (HepG2) | ICAM 1 expression | enhanced expresion vs control INFγ |

-continued

| IFNγ analog | Target receptor | Cells used | Parameter measured (details see text) | Results |
|---|---|---|---|---|
| Mannose-HSA-PEG-mimIFNγ | mannose receptor (CD 206) | Mouse RAW macrophages | MHC II expression | equal expression vs control INFγ |
| RGD-PEG-mimIFNγ | αvβ3 - receptor | Endothelial cells | In vitro angiogenesis assay | Enhanced effectivity vs control INFγ |

Experiments with Lactose-HSA-PEG-IFNγ:

Synthesis

Lactose-HSA (25 lactose molecules coupled to human serum albumin) was conjugated to bifunctional PEG molecule (2 KDa). Following dialysis, lactose-HSA-PEG was coupled to SATA-modified truncated IFNγ derived from mouse. The synthesized product (Lac-HSA-PEG-mimIFNγ) was extensively dialysed against PBS.

Experiment in Human Hepatocytes:

Human Hepatocytes (HepG2) were plated in 12 well plates ($1\times10^5$ cells/well). The cells were grown overnight in 5%/37° C./$CO_2$ incubator. Subsequently, cells were incubated with medium, mouse IFNγ (1 ug/ml), Human IFNγ (1 ug/ml), mouse IFNγ derived Lac-HSA-PEG-IFNγ (1 ug/ml), Lac-HSA or Lac-HSA-PEG-IFNγ (1 ug/ml) after 2 hrs of blocking with Lac-HSA. After 24 hrs of incubation, cells were lysed, RNA was isolated and reverse transcribed. The cDNA was used for the analysis of Inter-Cellular Adhesion Molecule 1 (ICAM1) expression, which is known to be induced in response to IFNγ. 18srRNA was used a housekeeping control.

Results:

As expected, neither mouse truncated IFNγ nor Lac-HSA induced ICAM1 expression in human hepatocytes, while both human IFNγ and mouse derived Lac-HSA-PEG-IFNγ upregulated ICAM1 expression in human hepatocytes. Furthermore, Lac-HSA-PEG-IFNγ-induced ICAM1 expression was almost completely blocked by excess of Lac-HSA.

Conclusions:

The species-specificity of $INF_Y$ was confirmed by showing that mouse (truncated) $INF_Y$ was ineffective in human hepatocytes. However, this cytokine was turned into a bioactive compound in human cells after coupling to the target moiety lactose, which is known to enter hepatocytes via the Asialoglycoprotein (ASGP) receptor. Specificity for the ASGP-receptor was shown by blockade of this receptor by Lac-HSA. This demonstrates that the signaling part of $INF_Y$ (which is not species specific) can be delivered into the cytoplasm of other target cells than fibroblasts via another target receptor than the PDGF-receptor using a sugar moiety instead of a peptide. Hepatocyte targeting is particularly relevant for the treatment of Hepatitis B and C and ICAM-1 upregulation is a physiological response to enhance antiviral activity. This experiment supports the use of cell-specific-truncated $INF_Y$ according to the invention as an antiviral compound.

Similarly, mannose was coupled to truncated mouse $INF_Y$ according to standard techniques (L. Beljaars et al J. of Hepatology 29: 579-588, 1998) and bioactivity of this mannosylated $INF_Y$ was demonstrated in mouse macrophages with MHC class II expression as read-out parameters (rtPCR methods).

The endothelial binding peptide RGD—or its control peptide RAG, that does not bind to these cells, were also coupled to truncated mouse $INF_Y$ according to standard methods. The resulting analogs were evaluated for their biological activity in cultures of endothelial cells (H5V) by measuring tube formation which is a parameter reflecting angiogenesis. Tube formation by H5V cells was inhibited most potently by RGD-mim$INF_Y$ in this assay (data not shown).

Conclusions:

Modification of truncated mouse $INF_Y$ by conjugation to a targeting moiety (e.g. an oligosaccharide or peptide) is feasible without disturbing the bioactivity of the signaling part of this cytokine. Delivery of an $INF_Y$ analog which is defective in binding to its natural receptor but which instead can bind to a distinct cell surface receptor mediating cellular uptake of the analog allows for more effective therapeutic applications with less side-effects.

References 1. du Bois R M. Strategies for treating idiopathic pulmonary fibrosis. Nat Rev Drug Discov; 9(2):129-40.
2. Wilson M S, Wynn T A. Pulmonary fibrosis: pathogenesis, etiology and regulation. Mucosal Immunol 2009; 2(2): 103-21.
3. Scotton C J, Chambers R C. Molecular targets in pulmonary fibrosis: the myofibroblast in focus. Chest 2007; 132 (4):1311-21.
4. Bonner J C. Mesenchymal cell survival in airway and interstitial pulmonary fibrosis. Fibrogenesis Tissue Repair; 3:15.
5. King T E, Jr., Albera C, Bradford W Z, et al. Effect of interferon gamma-1b on survival in patients with idiopathic pulmonary fibrosis (INSPIRE): a multicentre, randomised, placebo-controlled trial. Lancet 2009; 374(9685):222-8.
6. Beljaars L, Weert B, Geerts A, Meijer D K, Poelstra K. The preferential homing of a platelet derived growth factor receptor-recognizing macromolecule to fibroblast-like cells in fibrotic tissue. Biochemical pharmacology 2003; 66(7):1307-17.
7. Homma S, Nagaoka I, Abe H, et al. Localization of platelet-derived growth factor and insulin-like growth factor I in the fibrotic lung. Am J Respir Crit Care Med 1995; 152(6 Pt 1):2084-9.
8. Paakko P, Anttila S, Sormunen R, et al. Biochemical and morphological characterization of carbon tetrachloride-induced lung fibrosis in rats. Arch Toxicol 1996; 70(9):540-52.
9. Mizuguchi S, Takemura S, Minamiyama Y, et al. 5-allyl cysteine attenuated CCl4-induced oxidative stress and pulmonary fibrosis in rats. Biofactors 2006; 26(1):81-92.

Example 11

Binding Study of BiPPB to Cultured or Freshly Isolated Primary Cells

This example shows that Bi-PPB either produced chemically or through recombinant techniques specifically binds to the PDGFβ-receptor. Receptor specificity is demonstrated by blocking the binding with specific antiPDGF-β-receptor antibodies. BiPPB is species non-specific as it binds to Myofibroblast-like cells of rat, mouse and human. Receptor interaction requires at least two cyclic peptides, as the monocyclic form does not bind to the target receptor.

Sequence of BiPPB:

```
C(1)S R N L I D C(1)G G G D G G C(2)S R N L I D C(2)(SEQ ID NO: 59):

Cys(1)-Cys(1) and Cys(2)-Cys(2) disulfide bridge cyclisations
```

Methods:

The binding of BiPPB was performed in primary freshly isolated rat hepatic stellate cells. Cells were seeded in the 8-well glass plates (Lab-Tek, Nunc, Naperville, Ill.) at 30,000 cells/well in the culture medium. After overnight incubation at 37° C./5% CO2, cells were washed with PBS and subsequently incubated with FITC-labeled PPB (monocyclic) or BiPPB (bicyclic: 10 μg/ml) at room temperature. To block the binding, anti-PDGF-βR IgG was added to the cells 1 h before FITC coupled PPB or BiPPB. After 2 h, cells were washed 3 to 4 times with cold PBS and fixed with 4% paraformaldehyde. The nuclei were counterstained with DAPI and mounted in citifluor (anti-fade reagent) and visualized under fluorescent microscope.

Similar binding experiments were performed in primary freshly isolated human myofibroblasts, mouse 3T3 fibroblasts and human hepatic stellate cells (LX2). For human Hepatic stellate cells, the sequence of BiPPB was as follows:

```
C(1)S R N L I D C(1) KGSGSGG C(2)S R N L I D C(2)(SEQ ID NO: 60):

Cys(1)-Cys(1) and Cys(2)-Cys(2) disulfide bridge cyclisations
```

Results:

The FITC-coupled monocyclic PPB did not show any binding as the PDGF-receptor requires dimeric interaction. FITC-coupled BiPPB showed significant binding to the cell type tested, which was almost completely blocked by PDGF receptor antibody, showing the receptor specificity of the binding to these cells (data not shown).

The invention claimed is:

1. An analog of interferon gamma (IFNγ) the analog comprising the amino acid sequence set forth in SEQ ID NO: 56 or the amino acid sequence set forth in SEQ ID NO: 58.

2. The analog according to claim 1, further comprising at least one non-antigenic polymer.

3. A pharmaceutical composition comprising an analog according to claim 1 and a pharmaceutically acceptable carrier, adjuvant and/or excipient.

* * * * *